United States Patent
Bottaro et al.

(10) Patent No.: US 8,617,831 B2
(45) Date of Patent: Dec. 31, 2013

(54) METHODS FOR DIAGNOSING AND MONITORING THE PROGRESSION OF CANCER BY MEASURING SOLUBLE C-MET ECTODOMAIN

(71) Applicants: Donald P. Bottaro, Kensington, MD (US); Gagani P. Athauda, Miramar, FL (US); Teresa Lynn Burgess, Ventura, CA (US)

(72) Inventors: Donald P. Bottaro, Kensington, MD (US); Gagani P. Athauda, Miramar, FL (US); Teresa Lynn Burgess, Ventura, CA (US)

(73) Assignees: The United States of America, as Represented by the Secretary, Department of Health and Human Services, Washington, DC (US); Amgen, Inc., Thousand Oaks, CA (US)

( * ) Notice: Subject to any disclaimer, the term of this patent is extended or adjusted under 35 U.S.C. 154(b) by 0 days.

(21) Appl. No.: 13/627,595

(22) Filed: Sep. 26, 2012

(65) Prior Publication Data

US 2013/0029352 A1 Jan. 31, 2013

Related U.S. Application Data

(60) Continuation of application No. 13/053,560, filed on Mar. 22, 2011, now Pat. No. 8,304,199, which is a division of application No. 12/093,012, filed as application No. PCT/US2006/043654 on Nov. 8, 2006, now Pat. No. 7,964,365.

(60) Provisional application No. 60/734,993, filed on Nov. 8, 2005, provisional application No. 60/780,626, filed on Mar. 9, 2006.

(51) Int. Cl.
*G01N 33/53* (2006.01)

(52) U.S. Cl.
USPC ............................................. 435/7.2; 435/4

(58) Field of Classification Search
USPC ........................................................ 435/7.2, 4
See application file for complete search history.

(56) References Cited

FOREIGN PATENT DOCUMENTS

WO    WO 2005/026361    3/2005
WO    WO 2006/056766    6/2006
WO    WO 2007/016367    2/2007

OTHER PUBLICATIONS

Aebi et al., "cDNA structures and regulation of two interferon-induced human Mx proteins," Mol. Cell Biol., Nov. 1989, 9(11), 5062-5072.

Athauda et al., "c-Met ectodomain shedding rate correlates with malignant potential," Clinical Cancer Research: An Official Journal of the American Association for Cancer Research, Jul. 2006, 12(14 Pt. 1), 4154-4162.
Bellinzona et al. "Biopolymer-mediated suramin chemotherapy in the treatment of experimental brain tumours," Acta Oncologica, 2004, 43(3), 259-263.
Birchmeier et al., "Developmental roles of HGF/SF and its receptor, the c-Met tyrosine kinase," Trends in Cell Biology, Oct. 1998, 8(10), 404-410.
Birchmeier et al., "Met, metastasis motility and more," Nat. Rev. Mol. Cell. Biol., Dec. 2003, 4(12), 915-925.
Birchmeier et al., "Role of HGF/SF and c-Met in morphogenesis and metastasis of epithelial cells," Ciba Found. Symp., 1997, 212, 230-240.
Blobel, C.P., "ADAMs: Key Components in EGFR Signalling and Development," Nat. Rev. Mol. Cell Biol., Jan. 2005, 6(1), 32-43.
Burgess et al., "Fully Human Monoclonal Antibodies to Hepatocyte Growth Factor with Therapeutic Potential against Hepatocyte Growth Factor/c-Met-Dependent Human Tumors," Cancer Res., Feb. 2006, 66(3), 1721-1729.
Castagnino et al., "Induction of tissue inhibitor of metalloproteinase-3 is a delayed early cellular response to hepatocyte growth factor," Oncogene, Jul. 1998, 17(4), 481-492.
Cheng et al., "Overexpression of c-met as a prognostic indicator for transitional cell carcinoma of the urinary bladder: a comparison with p53 nuclear accumulation," J. Clin. Oncol., Mar. 2002, 20(6), 1544-1550.
Christensen et al., "A Selective Small molecule inhibitor of c-Met kinases inhibits c-Met-dependent phenotypes in vitro and exhibits cytoreductive antitumor activity in vivo," Cancer Research, Nov. 2003, 63(21), 7345-7355.
Christensen et al., "c-Met as a target for human cancer and characterization of inhibitors for therapeutic intervention," Cancer Letters, Jul. 2005, 225(1), 1-26.
Chu et al., "Genetic abnormalities specifically associated with varying metastatic potential of prostate cancer cell lines as detected by comparative genomic hybridization," Cancer Genet Cytogenet, Jun. 2001, 127(2), 161-167.
Comoglio et al., "Scatter Factors and invasive growth," Seminars in Cancer Biology, Apr. 2001, 11(2), 153-165.
Crepaldi et al., "Generation of a truncated hepatocyte growth factor receptor in the endoplasmic reticulum," J. Biol. Chem., Jan. 1994, 269(3), 1750-1755.
Dharmawardana et al., "Soluble c-Met ectodomain detection in urologic malignancies," Proceedings of the American Association for Cancer Research Annual Meeting, Apr. 2005, 46, p. 656.
Dunsmore et al., "Mechanisms of hepatocyte growth factor stimulation of keratinocyte metalloproteinase production," J. Biol. Chem., Oct. 1996, 271(40), 24576-24582.
Funakoshi et al., "Hepatocyte growth factor: from diagnosis to clinical applications," Clin. Chim. Acta, Jan. 2003, 327(1-2), 1-23.
Furge et al., "Met receptor tyrosine kinase: enhanced signaling through adapter proteins," Oncogene, Nov. 2000, 19(49), 5582-5589.
Galvani et al., "Suramin modulates cellular levels of hepatocyte growth factor receptor by inducing shedding of a soluble form," Biochem. Pharmacol., Sep. 1995, 50(7), 959-966.
Huh et al., "Hepatocyte growth factor/c-met signaling pathway is required for efficient liver regeneration and repair," PNAS, Mar. 2004, 101(13), 4477-4482.

(Continued)

*Primary Examiner* — Bin Shen
(74) *Attorney, Agent, or Firm* — Woodcock Washburn LLP

(57) ABSTRACT

Methods for measuring c-Met levels in urine and blood samples are provided. Methods for diagnosis and prognosis evaluation for cancer are also provided.

16 Claims, 13 Drawing Sheets

(56) References Cited

OTHER PUBLICATIONS

Jeffers et al., "Degradation of the Met tyrosine kinase receptor by the ubiquitin-proteasome pathway," Mol. Cell Biol., Feb. 1997, 17(2), 799-808.

Jeffers et al., "Enhanced tumorigenicity and invasion-matastasis by hepatocyte growth factor/scatter factor-met signalling in human cells concomitant with induction of the urokinase proteolysis network," Mol. Cell Biol., Mar. 1996, 16(3), 1115-1125.

Jin et al., "Early treatment with hepatocyte growth factor improves cardiac function in experimental heart failure induced by myocardial infarction," J. Pharmacol. Exp. Ther., Feb. 2003, 304(2), 654-660.

Joseph et al., "Expression of Scatter factor in human bladder carcinoma," J of the National Cancer Institute, Mar. 1995, 87(5), 372-377.

Komada et al "Proteolytic processing of the hepatocyte growth factor/scatter factor receptor by furin, " FEBS Letters, Aug. 1993, 328(1-2), 25-29.

Koochekpour et al., Met and hepatocyte growth factor/scatter factor expression in human gliomas, Cancer Res., Dec. 1997, 57(23), 5391-5398.

Leone et al., "Transfection of human nm23-H1 into the human MDA-MB-435 breast carcinoma cell line: effects on tumor metastatic potential, colonization and enzymatic activity," Oncogene, Sep. 1993, 8(9), 2325-2333.

Liu, Y., "Hepatocyte growth factor in kidney fibrosis: therapeutic potential and mechanisms of action," Am. J. Phys. Renal Physiol., Jul. 2004, 287(1), F7-16.

Masson et al., "Tumor necrosis factor receptor-associated periodic syndrome (TRAPS): definition, semiology, prognosis, pathogenesis, treatment, and place relative to other periodic joint diseases," Joint Bone Sprine, Jul. 2004, 71(4), 284-290.

Matsumoto et al., "Hepatocyte growth factor: renotropic role and potential therapeutics for renal diseases," Kidney International, Jun. 2001, 59(6), 2023-2028.

Michalopoulos et al., "Liver regeneration," Science, Apr. 1997, 276(5309), 60-66.

Nakamura et al., "Myocardial protection from ischemia/reperfusion injury by endogenous and exogenous HGF," J. Clin. Invest., Dec. 2000, 106(12), 1511-1519.

Nath et al., "Shedding of c-Met is regulated by crosstalk between a G-protein couple receptor and the EGF receptor and is mediated by a TIMP-3 sensitive metalloproteinase," J. Cell. Sci., Mar. 2001, 114(Pt. 6), 1213-1220.

Parr et al., "Expression of hepatocyte growth factor/scatter factor, its activator, inhibitors and the c-Met receptor in human cancer cells," International Journal of Oncology, Editorial Academy of the International Journal of Oncology, Oct. 2001, 19(4), 847-863.

Pennacchietti et al., "Hypoxia promotes invasive growth by transcriptional activation of the met protooncogene," Cancer Cell, Apr. 2003, 3(4), 347-361.

Pisters et al., "c-Met proto-oncogene expression in benign and malignant human prostate tissues," J. of Urology, Jul. 1995, 154(1), 293-298.

Prat et al., "C-terminal truncated forms of Met, the hepatocyte growth factor receptor," Mol. Cell. Biol., Dec. 1991, 11(12), 5954-5962.

Rosario et al., "How to make tubes: signalling by the met receptor tyrosine kinase," Trends Cell Biol., Jun. 2003, 13(6), 328-335.

Rosen et al., "Urinary and tissue levels of scatter factor in transitional cell carcinoma of bladder," J. Urol., Jan. 1997, 157(1), 72-78.

Salerno et al., "Inhibition of signal transduction by the nm23 metastasis suppressor: Possible mechanisms," Clin. Exp. Metastasis, 2003, 20(1), 3-10.

Santer et al., "Malignant MCF10CA1 cell lines derived from premalignant human breast epithelial MCF10AT cells," Breast Cancer Res. Treat., Jan. 2001, 65(2), 101-110.

Schmidt et al., "Scatter factor/hepatocyte growth factor is essential for liver development," Nature, Feb. 1995, 373(6516), 699-702.

Stahl et al., "Functional and biophysical characterization of recombinant human hepatocyte growth factor isoforms produced in *Escherichia coli*," Biochem J., Sep. 1997, 326(Pt. 3), 763-772.

Tang et al., "TGF-beta switches from tumor suppressor to prometastatic factor in a model of breast cancer progression," J. Clinical Invest., Oct. 2003, 112(7), 1116-1124.

Uehara et al., "Placental defect and embryonic lethality in mice lacking hepatocyte growth factor/scatter factor," Nature, Feb. 1995, 373, 702-705.

Wajih et al., "Vascular origin if a soluble truncated form of the hepatocyte growth factor receptor (c-Met)," Circulation Research, Grune and Stratton, Jan. 2002, 90(1), 46-52.

Wallenius et al., "Overexpression of the hepatocyte growth factor (HGF) receptor (MET) and presence of a truncated and activated intracellular HGF receptor fragment in locally aggressive/malignant human musculoskeletal tumors," Am. J. Pathol., Mar. 2000, 156(3), 821-829.

Wang et al., "Alteration of APC, c-met and p53 genes in tumor tissue and serum of patients with gastric cancers," J. of Surgical Research, Aug. 2004, 120(2), 242-248.

Yu et al., "Frequency of TPR-MET rearrangement in patients with gastric carcinoma and in first-degree relatives," Cancer, Apr. 2000, 88(8), 1801-1806.

c-Met Extracellular Domain

```
                    signal peptide          25  α-chain                           57 sema domain
  1  MKAPAVLAPG  ILVLLFTLVQ  RSNGECKEAL  AKSEMNVNMK  YQLPNFTAET  PIQNVILHEH  HIFLGATNYI   70

71  YVLNEEDLQK  VAEYKTGPVL  EHPDCFPCQD  CSSKANLSGG  VWKDNINMAL  VVDTYYDDQL  ISCGSVNRGT  140

141  CQRHVFPHNH  TADIQSEVHC  IFSPQIEEPS  QCPDCVVSAL  GAKVLSSVKD  RFINFFVGNT  INSSYFPDHP  210

211  LHSISVRRLK  ETKDGFMFLT  DQSYIDVLPE  FRDSYPIKYV  HAFESNNFIY  FLTVQRETLD  AQTFHTRIIR  280
                 α-chain  303  308  β-chain
281  FCSINSGLHS  YMEMPLECIL  TEKRKKRSTK  KEVFNILQAA  YVSKPGAQLA  RQIGASLNDD  ILFGVFAQSK  350

351  PDSAEPMDRS  AMCAFPIKYV  NDFFNKIVNK  NNVRCLQHFY  GPNHEHCFNR  TLLRNSSGCE  ARRDEYRTEF  420

421  TTALQRVDLF  MGQFSEVLLT  SISTFIKGDL  TIANLGTSEG  RFMQVVVSRS  GPSTPHVNFL  LDSHPVSPEV  490
     sema domain 500                                        plexin repeat
491  IVEHTLNQNG  YTLVITGKKI  TKIPLNGLG   RHFQ  SQ    SAPPFVQ      DK  VRSEE    LSGTWTQQI  560
                                                 IPT region 1
561  CLPA    VT  NSA  EGGT   L  CG DFG         RPNN KFDLKK  RV LKGNSSC  T  SQ H   KC VG    630

631  NK FNMS     SNGH T YS   T S VD PVIT  SISPKYGPMA  GGTLLTLTGN  YLNSGNSRHI  SIGGKTCTLK  700
                                                                TIG domain
701  SVSNSILECY  TPAQTISTEF  AVKLKIDLAN  RETSIFSYR   DPIVYEIHPT  KSFISTWWKE  PLNIVSFLFC  770
                                                IPT region 2
771  FASGGSTITG  VGKNLNSVSV  PRMVINVHEA  GRNFTVACQH  RSNSEIICCT  TPSLQQLNLQ  LPLKTKAFFM  840

841  LDGILSKYFD  ITVVHNPVFK  PFEKPVMISM  GNENVLEIKG  NDIDPEAVKG  EVLKVGNKSC  ENIHLHSEAV  910
                                            transmembrane domain
911  LCTVPNDLLK  LNSELNIEWK  QA SS VLGK  VI VG IONFT  GLTAG VVSIS  TALLLLLGFF  LWLKKRKQIK  980
```

PRIOR ART

Figure 10

Full length c-Met AA sequence

```
   1  MKAPAVLAPG ILVLLFTLVQ RSNGECKEAL AKSEMNVNMK YQLPNFTAET PIQNVILHEH HIFLGATNYI
  71  YVLNEEDLQK VAEYKTGPVL EHPDCFPCQD CSSKANLSGG VWKDNINMAL VVDTYYDDQL ISCGSVNRGT
 141  CQRHVFPHNH TADIQSEVHC IFSPQIEEPS QCEDCVVSAL GAKVLSSVKD RFINFFVGNT INSSYFPDHP
 211  LHSISVRRLK ETKDGFMFLT DQSYIDVLPE FRDSYPIKYV HAFESNNFIY FLTVQRETLD AQTFHTRIIR
 281  FCSINSGLHS YMEMPLECIL TEKRKKRSTK KEVFNILQAA YVSKPGAQLA RQIGASLNDD ILFGVFAQSK
 351  PDSAEPMDRS AMCAFPIKYV NDFFNKIVNK NNVRCLQHFY GPNHEHCFNR TLLRNSSGCE ARRDEYRTEF
 421  TTALQRVDLF MGQFSEVLLT SISTFIKGDL TIANLGTSEG REMQVVVSRS GPSTPHVNFL LDSHPVSPEV
 491  IVEHTLNQNG YTLVITGKKI TKIPLNGLGC RHFQSCSQCL SAPPFVQCGW CHDKCVRSEE CLSGTWTQQI
 561  CLPAIYKVFP NSAPLEGGTR LTICGWDFGF RRNNKFDLKK TRVLLGNESC TLTLSESTMN TLKCTVGPAM
 631  NKHFNMSIII SNGHGTTQYS TFSYVDPVII SISPKYGPMA GGTLLITLTGN YLNSGNSRHI SIGGKTCTLK
 701  SVSNSILECY TPAQTISTEF AVKLKIDLAN RETSIFSYRE DPIVYEIHPT KSFISTWWKE PLNIVSFLFC
 771  FASGGSTITG VGKNLNSVSV PRMVINVHEA GRNFTVACQH RSNSEIICCT TPSLQQLNLQ LPLKTKAFFM
 841  LDGILSKYFD LIYVHNPVFK PFEEKPVMSM GNENVLEIKG NDIDPEAVKG EVLKVGNKSC ENIHLHSEAV
 911  LCTVPNDLLK INSELNIEWK QAISSTVLGK VIVQPDQNFT GLIAGVVSIS TALLLLLGFF LWLKKRKQIK
 981  DLGSELVRYD ARVHTPHLDR LVSARSVSPT TEMVSNESVD YRATFPEDQF PNSSQNGSCR QVQYPLTDMS
1051  PILTSGDSDI SSPLLQNTVH IDLSALNPEL VQAVQHVVIG PSSLIVHFNE VIGRGHFGCV YHGTLLDNDG
1121  KKIHCAVKSL NRITDIGEVS QFLTEGIIMK DFSHPNVLSL LGICLRSEGS PLVVLPYMKH GDLRNFIRNE
1191  THNPTVKDLI GFGLQVAKAM ESLQTQKFTT KYLASKKFVH RDLAARNCML DEKFTVKVAD FGLARDMYDK EYYSVHNKTG
1261  AKLPVKWMAL ESLQTQKFTT KSDVWSFGVV LWELMTRGAP PYPDVNTFDI TVYLLQGRRL LQPEYCPDPL
1331  YEVMLKCWHP KAEMRPSFSE LVSRISAIFS TFIGEHVYHV NATYVNVKCV APYPSLLSSE DNADDEVDTR
1401  PASFWETS
```

Figure 11

SEQUENCE LISTING

<160> NUMBER OF SEQ ID NOS: 2

<210> SEQ ID NO 1
<211> LENGTH: 980
<212> TYPE: PRT

<213> ORGANISM: Artificial Sequence
<220> FEATURE:
<223> OTHER INFORMATION: Synthetic construct

<400> SEQUENCE: 1

```
Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Asn Val Arg
370                 375                 380

Cys Leu Gln His Phe Tyr Gly Pro Asn His Glu His Cys Phe Asn Arg
385                 390                 395                 400
```

-continued

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
                420                 425                 430

Gln Phe Ser Glu Val Leu Leu Thr Ser Ile Ser Thr Phe Ile Lys Gly
                435                 440                 445

Asp Leu Thr Ile Ala Asn Leu Gly Thr Ser Glu Gly Arg Phe Met Gln
            450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
                500                 505                 510

Ile Pro Leu Asn Gly Leu Gly Cys Arg His Phe Gln Ser Cys Ser Gln
            515                 520                 525

Cys Leu Ser Ala Pro Pro Phe Val Gln Cys Gly Trp Cys His Asp Lys
530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
                580                 585                 590

Asn Asn Lys Phe Asp Leu Lys Lys Thr Arg Val Leu Leu Gly Asn Glu
            595                 600                 605

Ser Cys Thr Leu Thr Leu Ser Glu Ser Thr Met Asn Thr Leu Lys Cys
    610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
            660                 665                 670

Thr Leu Leu Thr Leu Thr Gly Asn Tyr Leu Asn Ser Gly Asn Ser Arg
            675                 680                 685

His Ile Ser Ile Gly Gly Lys Thr Cys Thr Leu Lys Ser Val Ser Asn
    690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
            740                 745                 750

Phe Ile Ser Thr Trp Trp Lys Glu Pro Leu Asn Ile Val Ser Phe Leu
            755                 760                 765

Phe Cys Phe Ala Ser Gly Gly Ser Thr Ile Thr Gly Val Gly Lys Asn
    770                 775                 780

Leu Asn Ser Val Ser Val Pro Arg Met Val Ile Asn Val His Glu Ala
785                 790                 795                 800

Gly Arg Asn Phe Thr Val Ala Cys Gln His Arg Ser Asn Ser Glu Ile
                805                 810                 815

Ile Cys Cys Thr Thr Pro Ser Leu Gln Gln Leu Asn Leu Gln Leu Pro

```
                        820                 825                 830
Leu Lys Thr Lys Ala Phe Phe Met Leu Asp Gly Ile Leu Ser Lys Tyr
    835                 840                 845

Phe Asp Leu Ile Tyr Val His Asn Pro Val Phe Lys Pro Phe Glu Lys
    850                 855                 860

Pro Val Met Ile Ser Met Gly Asn Glu Asn Val Leu Glu Ile Lys Gly
865                 870                 875                 880

Asn Asp Ile Asp Pro Glu Ala Val Lys Gly Glu Val Leu Lys Val Gly
                    885                 890                 895

Asn Lys Ser Cys Glu Asn Ile His Leu His Ser Glu Ala Val Leu Cys
                900                 905                 910

Thr Val Pro Asn Asp Leu Leu Lys Leu Asn Ser Glu Leu Asn Ile Glu
                915                 920                 925

Trp Lys Gln Ala Ile Ser Ser Thr Val Leu Gly Lys Val Ile Val Gln
    930                 935                 940

Pro Asp Gln Asn Phe Thr Gly Leu Ile Ala Gly Val Val Ser Ile Ser
945                 950                 955                 960

Thr Ala Leu Leu Leu Leu Leu Gly Phe Phe Leu Trp Leu Lys Lys Arg
                    965                 970                 975

Lys Gln Ile Lys
            980

<210> SEQ ID NO 2
<211> LENGTH: 1408
<212> TYPE: PRT
<213> ORGANISM: Artificial Sequence
<220> FEATURE:
<223> OTHER INFORMATION: Synthetic construct

<400> SEQUENCE: 2

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
                20                  25                  30

Ser Glu Met Asn Val Asn Met Lys Tyr Gln Leu Pro Asn Phe Thr Ala
            35                  40                  45

Glu Thr Pro Ile Gln Asn Val Ile Leu His Glu His His Ile Phe Leu
        50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205
```

```
His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Asn Val Arg
    370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
            420                 425                 430

Gln Phe Ser Glu Val Leu Leu Thr Ser Ile Ser Thr Phe Ile Lys Gly
        435                 440                 445

Asp Leu Thr Ile Ala Asn Leu Gly Thr Ser Glu Gly Arg Phe Met Gln
    450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
        515                 520                 525

Cys Leu Ser Ala Pro Pro Phe Val Gln Cys Gly Trp Cys His Asp Lys
    530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
        595                 600                 605

Ser Cys Thr Leu Thr Leu Ser Glu Ser Thr Met Asn Thr Leu Lys Cys
    610                 615                 620

Thr Val Gly Pro Ala Met Asn Lys His Phe Asn Met Ser Ile Ile Ile
```

-continued

```
            625                 630                 635                 640
Ser Asn Gly His Gly Thr Thr Gln Tyr Ser Thr Phe Ser Tyr Val Asp
                    645                 650                 655

Pro Val Ile Thr Ser Ile Ser Pro Lys Tyr Gly Pro Met Ala Gly Gly
                660                 665                 670

Thr Leu Leu Thr Leu Thr Gly Asn Tyr Leu Asn Ser Gly Asn Ser Arg
                675                 680                 685

His Ile Ser Ile Gly Gly Lys Thr Cys Thr Leu Lys Ser Val Ser Asn
            690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
                740                 745                 750

Phe Ile Ser Thr Trp Trp Lys Glu Pro Leu Asn Ile Val Ser Phe Leu
                755                 760                 765

Phe Cys Phe Ala Ser Gly Gly Ser Thr Ile Thr Gly Val Gly Lys Asn
            770                 775                 780

Leu Asn Ser Val Ser Val Pro Arg Met Val Ile Asn Val His Glu Ala
785                 790                 795                 800

Gly Arg Asn Phe Thr Val Ala Cys Gln His Arg Ser Asn Ser Glu Ile
                805                 810                 815

Ile Cys Cys Thr Thr Pro Ser Leu Gln Gln Leu Asn Leu Gln Leu Pro
                820                 825                 830

Leu Lys Thr Lys Ala Phe Phe Met Leu Asp Gly Ile Leu Ser Lys Tyr
            835                 840                 845

Phe Asp Leu Ile Tyr Val His Asn Pro Val Phe Lys Pro Phe Glu Lys
850                 855                 860

Pro Val Met Ile Ser Met Gly Asn Glu Asn Val Leu Glu Ile Lys Gly
865                 870                 875                 880

Asn Asp Ile Asp Pro Glu Ala Val Lys Gly Glu Val Leu Lys Val Gly
                885                 890                 895

Asn Lys Ser Cys Glu Asn Ile His Leu His Ser Glu Ala Val Leu Cys
                900                 905                 910

Thr Val Pro Asn Asp Leu Leu Lys Leu Asn Ser Glu Leu Asn Ile Glu
            915                 920                 925

Trp Lys Gln Ala Ile Ser Ser Thr Val Leu Gly Lys Val Ile Val Gln
            930                 935                 940

Pro Asp Gln Asn Phe Thr Gly Leu Ile Ala Gly Val Val Ser Ile Ser
945                 950                 955                 960

Thr Ala Leu Leu Leu Leu Leu Gly Phe Phe Leu Trp Leu Lys Lys Arg
                965                 970                 975

Lys Gln Ile Lys Asp Leu Gly Ser Glu Leu Val Arg Tyr Asp Ala Arg
                980                 985                 990

Val His Thr Pro His Leu Asp Arg  Leu Val Ser Ala Arg  Ser Val Ser
            995                 1000                1005

Pro Thr  Thr Glu Met Val Ser  Asn Glu Ser Val Asp  Tyr Arg Ala
    1010                1015                1020

Thr Phe  Pro Glu Asp Gln Phe  Pro Asn Ser Ser Gln  Asn Gly Ser
    1025                1030                1035

Cys Arg  Gln Val Gln Tyr Pro  Leu Thr Asp Met Ser  Pro Ile Leu
    1040                1045                1050
```

```
Thr Ser Gly Asp Ser Asp Ile Ser Ser Pro Leu Leu Gln Asn Thr
1055             1060            1065

Val His Ile Asp Leu Ser Ala Leu Asn Pro Glu Leu Val Gln Ala
1070             1075            1080

Val Gln His Val Val Ile Gly Pro Ser Ser Leu Ile Val His Phe
1085             1090            1095

Asn Glu Val Ile Gly Arg Gly His Phe Gly Cys Val Tyr His Gly
1100             1105            1110

Thr Leu Leu Asp Asn Asp Gly Lys Lys Ile His Cys Ala Val Lys
1115             1120            1125

Ser Leu Asn Arg Ile Thr Asp Ile Gly Glu Val Ser Gln Phe Leu
1130             1135            1140

Thr Glu Gly Ile Ile Met Lys Asp Phe Ser His Pro Asn Val Leu
1145             1150            1155

Ser Leu Leu Gly Ile Cys Leu Arg Ser Glu Gly Ser Pro Leu Val
1160             1165            1170

Val Leu Pro Tyr Met Lys His Gly Asp Leu Arg Asn Phe Ile Arg
1175             1180            1185

Asn Glu Thr His Asn Pro Thr Val Lys Asp Leu Ile Gly Phe Gly
1190             1195            1200

Leu Gln Val Ala Lys Ala Met Lys Tyr Leu Ala Ser Lys Lys Phe
1205             1210            1215

Val His Arg Asp Leu Ala Ala Arg Asn Cys Met Leu Asp Glu Lys
1220             1225            1230

Phe Thr Val Lys Val Ala Asp Phe Gly Leu Ala Arg Asp Met Tyr
1235             1240            1245

Asp Lys Glu Tyr Tyr Ser Val His Asn Lys Thr Gly Ala Lys Leu
1250             1255            1260

Pro Val Lys Trp Met Ala Leu Glu Ser Leu Gln Thr Gln Lys Phe
1265             1270            1275

Thr Thr Lys Ser Asp Val Trp Ser Phe Gly Val Val Leu Trp Glu
1280             1285            1290

Leu Met Thr Arg Gly Ala Pro Pro Tyr Pro Asp Val Asn Thr Phe
1295             1300            1305

Asp Ile Thr Val Tyr Leu Leu Gln Gly Arg Arg Leu Leu Gln Pro
1310             1315            1320

Glu Tyr Cys Pro Asp Pro Leu Tyr Glu Val Met Leu Lys Cys Trp
1325             1330            1335

His Pro Lys Ala Glu Met Arg Pro Ser Phe Ser Glu Leu Val Ser
1340             1345            1350

Arg Ile Ser Ala Ile Phe Ser Thr Phe Ile Gly Glu His Tyr Val
1355             1360            1365

His Val Asn Ala Thr Tyr Val Asn Val Lys Cys Val Ala Pro Tyr
1370             1375            1380

Pro Ser Leu Leu Ser Ser Glu Asp Asn Ala Asp Asp Glu Val Asp
1385             1390            1395

Thr Arg Pro Ala Ser Phe Trp Glu Thr Ser
1400             1405
```

METHODS FOR DIAGNOSING AND MONITORING THE PROGRESSION OF CANCER BY MEASURING SOLUBLE C-MET ECTODOMAIN

CROSS REFERENCE TO RELATED APPLICATIONS

This application is a continuation of U.S. application Ser. No. 13/053,560, filed Mar. 22, 2011, now U.S. Pat. No. 8,304,199, issued Nov. 6, 2012, which is a division of U.S. application Ser. No. 12/093,012, filed May 8, 2008, now U.S. Pat. No. 7,964,365, issued Jun. 21, 2011, which is the U.S. national stage of International Application Number PCT/US2006/043654, filed Nov. 8, 2006, which claims the benefit of U.S. Provisional Application Ser. No. 60/780,626, filed Mar. 9, 2006, and U.S. Provisional Application Ser. No. 60/734,993, filed Nov. 8, 2005, each of which is incorporated herein by reference in its entirety.

TECHNICAL FIELD

The present invention relates generally to the field of cancer and more specifically to cancer diagnosis and prognosis.

BACKGROUND

Many transmembrane proteins are proteolytically released from the cell surface by a process known as ectodomain shedding. Shedding occurs under normal physiologic conditions and can be increased in certain pathologies. Among the many receptors for which ectodomain shedding has been demonstrated is c-Met, the hepatocyte growth factor ("HGF") receptor tyrosine kinase (Komada et al., *FEBS Lett* 1993; 328:25-9, Wajih et al., *Circ Res* 2002; 90:46-52). HGF is a pleiotropic heparin-binding protein identified and isolated based on observations of its mitogenic activity on hepatocytes and epithelial cells, and independently identified and isolated based on observations of its ability to stimulate cell motility (scatter factor or SF). (Comoglio et al., *Semin Cancer Biol* 2001; 11:153-65, Funakoshi et al., *Clin Chim Acta* 2003; 327:1-23). HGF is typically produced by cells of mesenchymal origin and acts in a paracrine manner on a variety of cellular targets including epithelial and endothelial cells, hematopoietic cells, neurons and melanocytes during embryonic development and throughout adulthood, in normal and pathological processes (Birchmeier et al., *Nat Rev Mol Cell Biol* 2003; 4:915-25). HGF is essential for embryonic development, where it is involved in somite migration, limb bud and limb skeletal muscle formation, placenta formation (Schmidt et al., *Nature* 1995; 373:699-702, Uehara et al., *Nature* 1995:373:702-5) and later in organogenesis (Rosario et al., *Trends Cell Biol* 2003; 13:328-35), in neural development (Birchmeier et al., *Trends Cell Biol* 1998:8:404-10) and in tissue repair and regeneration (Jin et al., *J Pharmacol Exp Ther* 2003; 304:654-60, Huh et al., *Proc Natl Acad Sci USA* 2004; 101:4477-82). While the role of HGF in adult homeostasis is not yet completely understood, a growing body of evidence suggests that it is an endogenous tissue protective factor for several major organs and has potent antifibrotic activity (Liu, *Am J Physiol Renal Physiol* 2004; 287:F7-16).

The MET oncogene was isolated from a human osteogenic sarcoma cell line that had been chemically mutagenized in vitro. Transforming activity was due to a DNA rearrangement where sequences from the TPR (translocated promoter region) locus on chromosome 1 fused to sequences from the MET locus on chromosome 7 (TPR-MET) (Furge et al., *Oncogene* 2000; 19:5582-9). This rearrangement has been found in patients with gastric carcinoma (Yu et al., *Cancer* 2000; 88:1801-6). Isolation of the full-length MET proto-oncogene coding sequence revealed structural features of a membrane spanning receptor tyrosine kinase (Furge et al., *Oncogene* 2000; 19:5582-9). The identification of HGF as the natural ligand for c-Met and the identity of SF and HGF united a collection of findings demonstrating that a single receptor transduced multiple biological activities including motility, proliferation, survival and branching morphogenesis (Birchmeier et al., *Nat Rev Mol Cell Biol* 2003; 4:915-25). Activation of the c-Met intrinsic tyrosine kinase (TK) activity was required for all of these activities. Consistent with its relationship with HGF, c-Met is widely expressed early in development, deletion of the gene is embryonic lethal in mice, and widespread expression persists throughout adulthood (Birchmeier et al., id). Both HGF and c-Met are upregulated after kidney, liver or heart injury, suggestive of a general mechanism of protection against tissue damage, as well as one of tissue repair and regeneration (Matsumoto et al., *Kidney Int* 2001; 59:2023-38, Michalopoulos et al., *Science* 1997; 276:60-6, Nakamura et al., *J Clin Invest* 2000; 106:1511-9).

HGF and c-Met are implicated in a wide variety of human malignancies including colon, gastric, bladder, breast, kidney, liver, lung, head and neck, thyroid and prostate, but also sarcomas, hematological malignancies, melanoma and central nervous system (CNS) tumors (Birchmeier et al., *Nat Rev Mol Cell Biol* 2003; 4:915-25, Birchmeier et al., *Ciba Found Symp* 1997; 212:230-40). Through paracrine signaling, overexpression of ligand and/or receptor, autocrine loop formation and/or receptor mutation and gene rearrangement, this signaling pathway can enhance tumor cell growth, proliferation, survival, motility and invasion. Inappropriate c-Met signaling in disease can resemble, at least in part, developmental transitions between epithelial and mesenchymal cell types normally regulated by HGF. Among the many genes upregulated in response to activation of this pathway is that of the receptor itself, creating the potential for c-Met overexpression in otherwise normal target cells through persistent ligand stimulation; consistent with this, c-Met overexpression is widely observed in cancers of epithelial origin where paracrine delivery of HGF results in dysregulated signaling, whereas cells of mesenchymal origin that normally express HGF often acquire c-Met expression, and several sarcomas display autocrine c-Met signaling (Furge et al., *Oncogene* 2000; 19:5582-9). Importantly, the c-Met pathway activates a program of cell dissociation and increased cell motility coupled with increased protease production that has been shown to promote cellular invasion through extracellular matrices, and that closely resembles tumor metastasis in vivo (Birchmeier et al., *Ciba Found Symp* 71p 1997; 212:230-40). In addition, pathway activation in vascular cells stimulates tumor angiogenesis, facilitating tumor growth for cancers that are growth limited by hypoxia, and promoting tumor metastasis. Hypoxia alone upregulates c-Met expression and enhances HGF/SF signaling in cultured cells and mouse tumor models (Pennacchietti et al., *Cancer Cell* 2003; 3:347-61).

Early diagnosis is a key strategy in cancer treatment. Although it is known that c-Met is overexpressed in certain cancers, a need exists for a screening test for c-Met that is sensitive, cost-efficient, and can be used for diagnosis, determining stage of disease, prognosis, and/or assessing the efficacy of therapeutic intervention. The invention is directed to this and other ends.

SUMMARY

The present invention generally relates to methods for diagnosing cancer in a patient or methods for identifying a patient having an increased risk of developing cancer. The methods provide for analysis of patient samples to identify the presence of tumor cells in the patient due to the observation that tumor cells expressing c-Met shed more c-Met ectodomain than their normal tissue counterparts, independent of changes in overall c-Met expression levels, and that this shedding is enhanced with increasingly malignant phenotype. Moreover, the methods for diagnosis provide that c-Met ectodomain shedding can be quantitated in cell lysates, culture supernatants, and biological samples, such as blood and urine, and that c-Met levels are measurable before tumors become palpable yet correlate directly with tumor volume. Thus, it was concluded that for a variety of cancers, c-Met ectodomain shedding provides a reliable and practical indicator of, among other things, malignant potential and overall tumor burden.

A method for identifying a patient having an increased risk of developing cancer which comprises the steps of measuring an amount of soluble c-Met ectodomain in a biological sample of the patient; and detecting an increased concentration of soluble c-Met ectodomain in the biological sample when compared to the concentration of soluble c-Met ectodomain in a corresponding biological sample from a control population, wherein an increased concentration of soluble c-Met ectodomain identifies the patient as having an increased risk of developing cancer. The biological sample includes, but is not limited to, blood plasma or urine. The concentration of soluble c-Met ectodomain in a urine sample and a blood plasma sample is measured and the combined measurement can be used to determine if the patient has the increased risk of developing cancer. An increased concentration of soluble c-Met ectodomain can identify the patient as having an increased risk of developing metastatic cancer.

In one aspect, a soluble c-Met ectodomain level of about 3500 pg c-Met per mg urine creatinine or greater is indicative of an increased risk of developing cancer in the patient. In a further aspect, a soluble c-Met ectodomain level of about 4900 pg c-Met per mg urine creatinine or greater is indicative of an increased risk of developing cancer in the patient. In a further aspect, a soluble c-Met ectodomain level of about 3800 pg c-Met per mg urine creatinine or greater is indicative of an increased risk of developing cancer in the patient. In a detailed aspect, a soluble c-Met ectodomain level of about 4200 pg c-Met per mg urine creatinine or greater is indicative of an increased risk of developing cancer in the patient. In a detailed aspect, a soluble c-Met ectodomain level of about 4500 pg c-Met per mg urine creatinine or greater is indicative of an increased risk of developing cancer in the patient. The cancer diagnosis can be a cancer of the urinary tract. The cancer includes, but is not limited to, kidney cancer, renal cancer, prostate cancer, bladder cancer, renal cell carcinoma, or breast cancer.

A method for monitoring the progression of cancer in a patient is provided which comprises the steps of measuring an amount of soluble c-Met ectodomain in a first biological sample at a first time point, measuring an amount of soluble c-Met ectodomain in a second biological sample at a second time point, and determining progression of cancer in the patient based upon a change in amount of soluble c-Met ectodomain in the first biological sample compared to the second biological sample. The amount of soluble c-Met ectodomain in a urine sample or blood plasma sample, or a combination thereof, is measured and the combined measurement is used to determine the progression of cancer.

A method for measuring the response to cancer therapy in a patient is provided which comprises the steps of measuring an amount of soluble c-Met ectodomain in a biological sample of the patient at a first time point, measuring an amount of soluble c-Met ectodomain in a second biological sample of the patient at a second time point, and determining response to cancer therapy in the patient based upon the change in amount of soluble c-Met ectodomain in the first biological sample compared to the second biological sample. In one aspect, a decrease in the amount of soluble c-Met ectodomain in the first biological sample compared to the second biological sample indicates a positive response to cancer therapy in the patient. The cancer therapy can be an anti-cancer drug, for example, a chemotherapeutic agent, ionizing radiation therapy or hormone ablation therapy.

A method of assaying for an amount of c-Met ectodomain present in a biological sample from a human patient, said method is provided which comprises assaying the biological sample to determine an amount of c-Met ectodomain present in the biological sample from the patient, and comparing the amount of c-Met ectodomain present in the biological sample from the patient to an amount of c-Met ectodomain found in a biological sample of a control population, wherein an increase in the amount of c-Met ectodomain found in the sample of the patient compared to the amount of c-Met ectodomain found in the sample of the control population is indicative of the patient having cancer.

BRIEF DESCRIPTION OF THE DRAWINGS

FIG. 7 provides a column scattergram illustrating the c-Met values in human patient urine sample. The Y axis shows c-Met pg/mg creatinine. The following acronyms are used on the X (Category) axis: HLRCC refers to Hereditary Leiomyomatosis and Renal Cell Carcinoma (inherited kidney cancer syndrome); BPH refers to Benign Prostatic Hypertrophy (possibly prelude to prostate cancer); CaP refers to Prostate Cancer; CaB refers to Bladder Cancer; and PRC refers to Papillary Renal Cancer, sporadic, not inherited. Each data point is shown as a symbol. The horizontal line represents the median. Statistical analysis was not performed for this data set.

FIG. 8 provides a bar graph illustrating the mean values of c-Met in the patient populations. The Y axis shows c-Met pg/mg creatinine. The following acronyms are used on the X (Category) axis: HLRCC refers to Hereditary Leiomyomatosis and Renal Cell Carcinoma (inherited kidney cancer syndrome); BPH refers to Benign Prostatic Hypertrophy (possibly prelude to prostate cancer); CaP refers to Prostate Cancer; CaB refers to Bladder Cancer; and PRC refers to Papillary Renal Cancer, sporadic, not inherited. Statistical analysis was not performed for this data set.

FIG. 9 provides a bar graph illustrating normalized c-Met values over "No Malignancy group". The Y shows fold increase in c-Met. The following acronyms are used on the X (Category) axis: HLRCC refers to Hereditary Leiomyomatosis and Renal Cell Carcinoma (inherited kidney cancer syndrome); BPH refers to Benign Prostatic Hypertrophy (possibly prelude to prostate cancer); CaP refers to Prostate Cancer; CaB refers to Bladder Cancer; and PRC refers to Papillary Renal Cancer, sporadic, not inherited. Statistical analysis was not performed for this data set.

FIG. 10: Sequence for c-Met extracellular domain. FIG. 10 provides the sequence for the c-met extracellular domain, SEQ ID NO: 1 showing the functional domains. The c-Met ectodomain comprises residues 25 to 932 of the c-Met extracellular domain.

FIG. 11: c-Met full length sequence. FIG. 11 provides the full length c-Met sequence, SEQ ID NO:2.

FIG. 12 provides a box and whisker graph illustrating c-Met shedding in a group of normal patients versus patients with bladder cancer. The box extends from the $25^{th}$ percentile to the $75^{th}$ percentile, with a horizontal line at the median ($50^{th}$ percentile). Whiskers extend down to the smallest value and up the largest.

DETAILED DESCRIPTION OF ILLUSTRATIVE EMBODIMENTS

Overview

Figure 1:
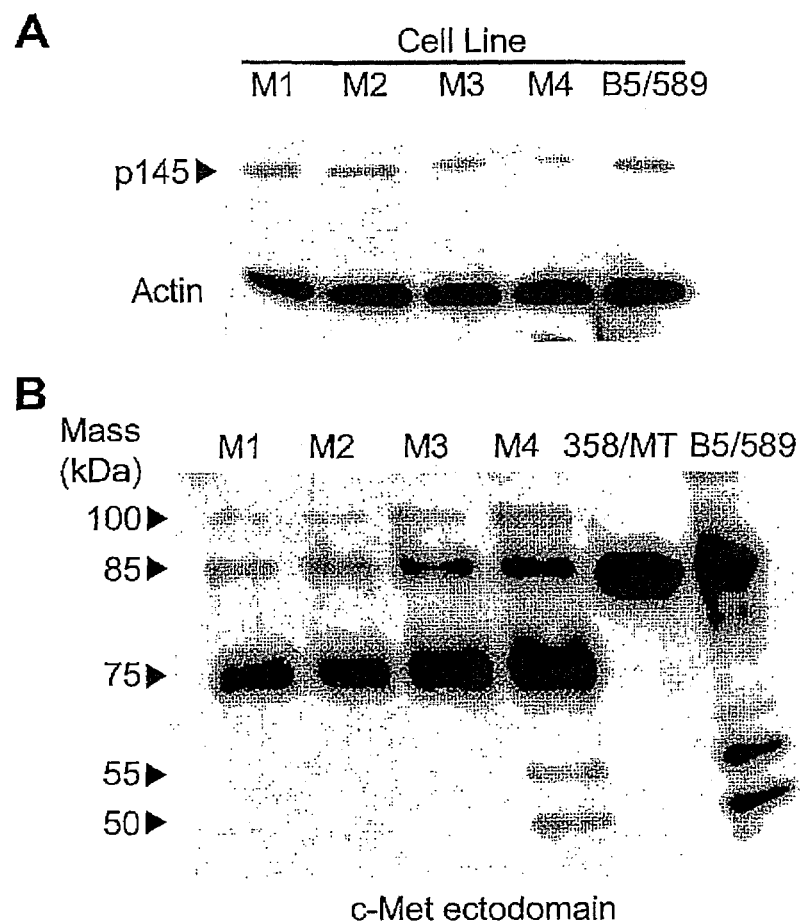
FIG. 1. c-Met shedding in a cultured cell model of breast tumor progression. 1A. Reducing SDS-PAGE and immunoblot analysis of the c-Met expression in four mammary cell lines; p145 is the intact c-Met beta subunit. In this model, M2, M3 and M4 represent derivatives of the normal breast cell line M1 with increasingly malignant phenotype. The normal mammary epithelial cell line B5/589 was used as a positive control for c-Met expression, and lysates were immunoblotted for beta actin to confirm equal sample loading. 1B. Reducing SDS-PAGE and immunoblot analysis of c-Met ectodomain shedding by cell lines M1, M2, M3 and M4. Culture supernatant from B5/589, as well as a purified recombinant c-Met ectodomain IgG Fc fusion protein (358-MT, R&D Systems) were used as positive controls of c-Met shedding and ectodomain recognition, respectively. Molecular masses of predominant c-Met ectodomain fragments are indicated in kDa at left.

The present inventors have observed, after analyzing patient samples, that tumor cells expressing c-Met shed more c-Met ectodomain than their normal tissue counterparts, independent of changes in overall c-Met expression levels, and that this shedding is enhanced with increasingly malignant phenotype. Moreover, the present inventors have observed, after further analysis, that c-Met ectodomain shedding can be quantitated in cell lysates, culture supernatants, and biological samples, such as blood and urine, and that c-Met levels are measurable before tumors become palpable yet correlate directly with tumor volume. Thus, it was concluded that for a variety of cancers, c-Met ectodomain shedding provides a reliable and practical indicator of, among other things, malignant potential and overall tumor burden. The observation and conclusion that c-Met can be detected in urine and provides a reliable and practical indicator of malignant potential and overall tumor burden was particularly surprising given the large size of the c-Met ectodomain, the low expression levels of c-Met, the acidic pH of urine, and the protease content in urine.

This invention provides, inter alia, methods and assays for diagnosing cancer in a subject, identifying a patient having an increased risk of developing cancer, monitoring the progression of cancer in a subject, measuring a clinical parameter related to cancer in subject, and measuring the therapeutic response to a cancer drug. In a particularly preferred embodiment, the present invention provides methods and assays for diagnosing bladder cancer in a subject, monitoring the progression of bladder cancer in a subject, measuring a clinical parameter related to bladder cancer in subject, and measuring the therapeutic response to a cancer drug for the treatment of bladder cancer.

"Cancer" refers to any of a number of diseases that are characterized by uncontrolled, abnormal proliferation of cells, as well as any of a number of characteristic structural and/or molecular features. A "cancerous cell" is understood as a cell having specific structural properties, lacking differentiation and in many instances, being capable of invasion and metastasis, see DeVita, V. et al. (eds.), 2001, *Cancer Principles and Practice of Oncology,* 6th. Ed., Lippincott Williams & Wilkins, Philadelphia, Pa.). The term cancer includes, for example, cancers of the female reproductive organs including, for example, ovarian cancer, cervical cancer and uterine cancer; lung cancer; breast cancer; renal cell carcinoma; Hodgkin's lymphoma; Non-Hodgkin's lymphoma; cancers of the genitourinary system including, for example, kidney cancer, prostate cancer, bladder cancer, and urethral cancer; cancers of the head and neck; liver cancer; cancers of the gastrointestinal system including, for example, stomach cancer, esophageal cancer, small bowel cancer or colon cancer; cancers of the biliary tree; pancreatic cancer; cancers of the male reproductive system including, for example, testicular cancer; Gestational trophoblastic disease; cancers of the endocrine system including, for example, thyroid cancer, parathyroid cancer, adrenal gland cancer, carcinoid tumors, insulinomas and PNET tumors; sarcomas, including, for example, Ewing's sarcoma, osteosarcoma, liposarcoma, leiomyosarcoma, and rhabdomyosarcoma; mesotheliomas; cancers of the skin; melanomas; cancers of the central nervous system; pediatric cancers; and cancers of the hematopoietic system including, for example, all forms of leukemia, myelodysplastic syndromes, myeloproliferative disorders and multiple myeloma. Cancers referred to in the present methods include those wherein the c-Met signaling pathway is overexpressed, accompanied by increased protease production and/or contributes to malignancy. Exemplary cancers include, for example urological cancers, such as bladder cancer; carcinomas, such as bladder, breast, cervical, cholangiocarcinoma, colorectal, oesophageal, gastric, head and neck, kidney, liver, lung, nasopharyngeal, ovarian, pancreas/gall bladder, prostrate and thyroid carcinomas; musculoskeletal carcinomas, such as, osteosarcoma, synovial sarcoma, and rhabdomyosarcoma; soft tissue sarcomas, such as, MFH/fibrosarcoma, leiomyosarcoma, and kaposi's sarcoma; haematopietic malignancies, such as, multiple myeloma, lymphomas, adult T-cell leukemia, acute myelogenous leukemia, and chronic myeloid leukemia; and other neoplasms, such as glioblastomas, astrocytomas, melanoma, mesothelioma, and Wilms' tumor (Birchmeier et al., *Nat Rev Mol Cell Bio* 2003 4(12):912-925.

In certain embodiments, the present invention provides methods of diagnosing cancer in a patient or methods for identifying a patient having an increased risk of developing cancer. Diagnosis, as used herein, includes not only the initial identification of a cancer associated with c-met ectodomain shedding in a patient but confirmatory testing, or screening in patients who have previously been identified as having or likely to have a cancer associated with c-met ectodomain shedding. The methods include the steps of providing a biological sample from the patient, measuring the amount of soluble c-Met ectodomain in the biological sample, preferably a urine and/or blood plasma sample, and determining if the patient has a greater likelihood of cancer based on the amount of c-Met measured. A patient has a greater likelihood of having cancer when he has a c-Met level that is greater than the mean c-Met level in a non-cancerous population.

In certain embodiments, a patient having a greater likelihood of cancer will have an amount of c-Met present in a biological sample, preferably a urine and/or plasma sample, that is at least two times the mean amount of c-Met present in a corresponding sample from a non-cancerous control population, at least three times the mean amount of c-Met present in a corresponding sample from a non-cancerous control population, at least four times the mean amount of c-Met present in a corresponding sample from a non-cancerous control population, or at least seven times the mean amount of c-Met present in a corresponding sample from a non-cancerous control population.

The present inventors have analyzed patient samples and after analysis concluded that the mean c-Met levels in a non-cancerous control population (n=30) is 4193 mg c-Met per mg urine creatinine with a standard error of 335. Further statistical analysis has shown that the lower 95% confidence level is 3508 mg c-Met per mg urine creatinine and the higher 95% confidence level is 4878 mg c-Met per mg urine creatinine. Accordingly, in certain embodiments of the present invention, a measurement of c-Met of about 3500 or greater, about 3800 or greater, about 4200 or greater, about 4500 or greater, or about 4900 c-Met per mg urine creatinine or greater, in a urine sample from a patient will be indicative of a greater likelihood of cancer in the patient. Similarly, a measurement of c-Met of less than about 3500 c-Met per mg urine creatinine will indicate that the patient has a smaller risk than the general population of having cancer.

The present inventors have analyzed the patient data and concluded that the mean c-Met levels in a population (n=12) having bladder cancer is 10,600 mg c-Met per mg urine creatinine with a standard error of 2678. Further statistical analysis has shown that the lower 95% confidence level is 4709 mg c-Met per mg urine creatinine and the higher lower 95% confidence level is 16,500 mg c-Met per mg urine creatinine. Accordingly, in certain embodiments of the present invention, a measurement of c-Met of about 4700 or greater, about 6000 or greater, about 7000 or greater or about 8000 or greater, c-Met per mg urine creatinine or greater, in a urine sample from a patient, will be indicative of a greater likelihood of having cancer, in particular bladder cancer A human sample value, obtained in triplicate or greater replicates, with a mean above the upper limit of the normal range (defined by the upper 95% Confidence Interval, or 4878 pg c-Met/mg Creatinine), and determined to be significantly different (as defined using the Student's t-test or other appropriate statistical analysis) from the normal mean presented herein (4193 pg c-Met/mg Creatinine), indicates a greater likelihood of having cancer or other hyperplastic disease, in particular bladder cancer.

A patient having a greater likelihood of having cancer can then be further screened to determine whether the subject does, in fact, have cancer. These screening methods include, for example, conventional work-ups to determine risk factors that are associated with cancer, a history and physical or neurological exam with particular attention to obvious lesions; palpable masses; ulcerations; swelling or enlargement of any masses or organs; erosion of bone; laterality; size and number of palpable lymph nodes; vision changes, focal deficit, tumor impingement on a specific nerve or structure; evidence of increased intracranial pressure; evidence of obstructive hydrocephalus. A diagnosis of cancer can be confirmed, for example, by imaging tests such as X-rays, nuclear scans and/or biopsies.

The methods of the invention rely, in part, on measuring the amount of c-Met in a sample. The c-met protooncogene is transmembrane protein that is derived from a 170 kDa precursor. The mature c-met protein is composed of a 50 KDa α subunit that is linked by 2 disulfide bonds to a 145 kDA β subunit. The c-Met ectodomain comprises residues 25 to 932 of the c-Met extracellular domain, SEQ ID NO: 1, as shown in FIG. 11.

As used herein, the phrase "measuring the amount of c-Met or soluble c-Met ectodomain" means any direct or indirect quantitative assay for c-Met ectodomain, including fragments thereof.

Biological sample refers to a biological tissue or biological fluid from a patient or human patient. The biological tissue can be assayed for c-Met ectodomain as a detergent extract of the tissue. Biological tissue from a patient can be extracted with non-ionic detergent buffer solutions as described herein for preparing cell extracts. The tissue can be minced or ground (at 4° C. or on ice) to maximize surface area available for extraction, and generally the extraction (also on ice) is performed for a much longer period (2-3 hours) as opposed to a few minutes for cultured cells.

A variety of biological samples can be useful in practicing the methods of the invention including, for example, blood, serum, plasma, urine, salivary fluid, ascite fluid and the like. A preferred biological sample is urine.

Such assays provide valuable means of monitoring the status of neoplastic diseases. In addition to improving prognostication, knowledge of the disease status allows the attending physician to select the most appropriate therapy for the individual patient. For example, patients with a high likelihood of relapse can be treated rigorously, usually involving systemic chemotherapy and/or radiation therapy. When there is a lesser likelihood of relapse, less aggressive therapies can be chosen. Because of the severe patient distress caused by the more aggressive therapy regimens, it would be desirable to distinguish with a high degree of certainty those patients requiring such aggressive therapies. See for example, U.S. Pat. No. 5,674,753, incorporated herein by reference in its entirety.

The present methods are useful for screening a wide variety of neoplastic diseases, including both solid tumors and hematopoietic cancers. Exemplary neoplastic diseases include carcinomas, such as adenocarcinomas and melanomas, and squamous cell carcinomas of the head and neck; mesodermal tumors, such as neuroblastomas and retinoblastomas; sarcomas, such as osteosarcomas, Ewing's sarcoma, and various leukemias; and lymphomas. Of particular interest are gynecologic cancers including ovarian, cervical, vaginal, endometrial and vulval cancers; gastrointestinal cancer, such as, stomach, colon and esophageal cancers; urinary tract cancer, such as, bladder and kidney cancers; skin cancer; liver cancer; prostate cancer; lung cancer; and breast cancer. Of still further particular interest are gynecologic cancers; breast cancer; urinary tract cancers, especially bladder cancer; lung cancer; gastrointestinal cancer, such as, stomach, colon and esophageal cancers; and liver cancer. Even further of particular interest are gynecologic cancers and breast cancer. Tumors which are known to overexpress intact c-Met may be good candidates for target neoplastic diseases for the assays of this invention, that is, such tumors may release into body fluids the c-Met ectodomain protein at elevated levels above normal. Particularly well studied are tumors of the breast and adenocarcinomas of the vulva which have been confirmed to overexpress c-Met. Preferably, in regard to tumors of the lung and cervix, squamous cell carcinomas have been particularly associated with elevated levels of c-Met. c-Met measurements have been determined to be markers for breast cancer and to provide valuable information diagnostically and prognostically, in correlation with other markers, such as, hormone receptor measurements, for example, with estrogen receptors (ERs) and progesterone receptors (PRs).

The body fluids that are of particular interest in assaying for the c-Met ectodomain protein according to the methods of this invention include blood, serum, semen, breast exudate, saliva, sputum, urine, cytosols, plasma, ascites, pleural effusions, amniotic fluid, bladder washes, bronchioalveolar lavages, and cerebrospinal fluid. Blood, serum, plasma, and urine are useful for screening according to the methods of this invention. The assays of this invention may also be useful in detecting and/or quantitating said c-Met ectodomain protein in tissue extracts.

From a knowledge of the structure of the external domain of the c-Met, a number of monoclonal or polyclonal antibodies can be generated that specifically recognize that protein. Because said c-Met ectodomain protein is found to exist freely in the biological fluids of mammals, it is possible to detect and/or quantitate the levels of that protein. Utilizing current antibody detection techniques that can quantitate the binding of monoclonal antibodies, made specifically to epitopes on the external domain of the c-Met, in particular to epitopes on the N-terminal, one can determine the amount of said c-Met ectodomain protein in the fluids of cancer patients.

Such an assay can be used to detect tumors, quantitate their growth, and help in the diagnosis and prognosis of the human disease. The assays can also be used to detect the presence of cancer metastasis, as well as confirm the absence or removal of all tumor tissue following surgery, cancer chemotherapy and/or radiation therapy. It can further be used to monitor cancer chemotherapy and tumor reappearance. Representative immunoassays involve the use of monoclonal or polyclonal antibodies which can be appropriately labeled to detect and/or quantitate said c-Met ectodomain protein in the body fluids of mammals.

Diagnosis is based on analyzing the sample for amount of c-Met and comparing it to a reference value, where the reference value serves to assist in differentiating those with cancer or a certain stage of cancer from other individuals. Statistical analysis routines can be performed to develop predictive models for identification of the different clinical parameters described herein. Measuring an "amount" in a sample means quantifying c-Met by determining, for example, the relative or absolute amount of protein.

A variety of assays for detecting c-Met are known in the art and include direct and indirect assays for c-Met protein. Immunoassays, including radioimmunoassays, enzyme-linked immunoassays and two-antibody sandwich assays as described further below, are useful in the methods of the invention. Furthermore, monoclonal and polyclonal anti-c-Met antibodies useful in immunoassays can be readily obtained from a variety of sources.

A variety of immunoassay formats, including competitive and non-competitive immunoassay formats, antigen capture assays and two-antibody sandwich assays also are useful the methods of the invention (Self and Cook, *Curr. Opin. Biotechnol.* 7:60-65 (1996)). In one embodiment, a method of the invention relies on one or more antigen capture assays. In an antigen capture assay, antibody is bound to a solid phase, and sample is added such that c-Met antigen is bound by the antibody. After unbound proteins are removed by washing, the amount of bound antigen can be quantitated, if desired, using, for example, a radioassay (Harlow and Lane, *Antibodies A Laboratory Manual* Cold Spring Harbor Laboratory: New York, 1988)). Immunoassays can be performed under conditions of antibody excess, or as antigen competitions, to quantitate the amount of antigen and, thus, determine a level of c-Met.

Enzyme-linked immunosorbent assays (ELISAs) can be useful in certain methods of the invention. An enzyme such as horseradish peroxidase (HRP), alkaline phosphatase (AP), β-galactosidase or urease can be linked, for example, to an anti-c-Met antibody or to a secondary antibody for use in a method of the invention. A horseradish-peroxidase detection system can be used, for example, with the chromogenic substrate tetramethylbenzidine (TMB), which yields a soluble product in the presence of hydrogen peroxide that is detectable at 450 nm. Other convenient enzyme-linked systems include, for example, the alkaline phosphatase detection system, which can be used with the chromogenic substrate p-nitrophenyl phosphate to yield a soluble product readily detectable at 405 nm. Similarly, a β-galactosidase detection system can be used with the chromogenic substrate o-nitrophenyl-β-D-galactopyranoside (ONPG) to yield a soluble product detectable at 410 nm, or a urease detection system can be used with a substrate such as urea-bromocresol purple (Sigma Immunochemicals, St. Louis, Mo.). Useful enzyme-linked primary and secondary antibodies can be obtained from a number of commercial sources such as Jackson Immuno-Research (West Grove, Pa.) as described further below.

In certain preferred embodiments, c-Met ectodomain is detected and measured using chemiluminescent detection. For example in certain embodiments, c-Met ectodomain specific antibodies are used to capture c-Met ectodomain present in the biological sample and a antibody specific for the c-Met ectodomain specific antibodies and labeled with an chemiluminescent label is used to detect the c-Met ectodomain present in the sample. Any chemiluminescent label and detection system can be used in the present methods. Chemiluminescent secondary antibodies can be obtained commercially from various sources such as Amersham. Methods of detecting chemiluminescent secondary antibodies are known in the art and are not discussed herein in detail.

Fluorescent detection also can be useful for detecting c-Met in certain methods of the invention. Useful fluorochromes include, without limitation, DAPI, fluorescein, Hoechst 33258, R-phycocyanin, B-phycoerythrin, R-phycoerythrin, rhodamine, Texas red and lissamine. Fluorescein or rhodamine labeled α 2-MG-, HA-, TIMP-1- or YKL-40-specific binding agents such as anti-α 2-MG, anti-HA, anti-TIMP-1, or anti-YKL-40 antibodies, or fluorescein- or rhodamine-labeled secondary antibodies can be useful in the invention. Useful fluorescent antibodies can be obtained commercially, for example, from Tago Immunologicals (Burlingame, Calif.) as described further below.

Radioimmunoassays (RIAs) also can be useful in certain methods of the invention. Such assays are well known in the art. Radioimmunoassays can be performed, for example, with $^{125}$I-labeled primary or secondary antibody (Harlow and Lane, supra, 1988).

A signal from a detectable reagent can be analyzed, for example, using a spectrophotometer to detect color from a chromogenic substrate; a radiation counter to detect radiation, such as a gamma counter for detection of $^{125}$I; or a fluorometer to detect fluorescence in the presence of light of a certain wavelength. Where an enzyme-linked assay is used, quantitative analysis of the amount of c-Met can be performed using a spectrophotometer such as an EMAX Microplate Reader (Molecular Devices; Menlo Park, Calif.) in accordance with the manufacturer's instructions. The assays of the invention can be automated or performed robotically, if desired, and that the signal from multiple samples can be detected simultaneously.

The methods of the invention also encompass the use of capillary electrophoresis based immunoassays (CEIA), which can be automated, if desired. Immunoassays also can be used in conjunction with laser-induced fluorescence as described, for example, in Schmalzing and Nashabeh, *Electrophoresis* 18:2184-93 (1997), and Bao, *J. Chromatogr. B. Boomed. Sci.* 699:463-80 (1997). Liposome immunoassays, such as flow-injection liposome immunoassays and liposome immunosensors, also can be used to detect c-Met or to determine a level of c-Met according to certain methods of the invention (Rongen et al., J. Immunol. Methods 204:105-133 (1997)).

Sandwich enzyme immunoassays also can be useful in certain methods of the invention. In a two-antibody sandwich assay, a first antibody is bound to a solid support, and the antigen is allowed to bind to the first antibody. The amount of c-Met is quantitated by measuring the amount of a second antibody that binds to it.

Quantitative western blotting also can be used to detect c-Met or to determine a level of c-Met in a method of the invention. Western blots can be quantitated by well known methods such as scanning densitometry. As an example, protein samples are electrophoresed on 10% SDS-PAGE Laemmli gels. Primary murine monoclonal antibodies, for example, against c-Met are reacted with the blot, and antibody binding confirmed to be linear using a preliminary slot blot experiment. Goat anti-mouse horseradish peroxidase-coupled antibodies (BioRad) are used as the secondary antibody, and signal detection performed using chemiluminescence, for example, with the Renaissance chemiluminescence kit (New England Nuclear; Boston, Mass.) according to the manufacturer's instructions. Autoradiographs of the blots are analyzed using a scanning densitometer (Molecular Dynamics; Sunnyvale, Calif.) and normalized to a positive control. Values are reported, for example, as a ratio between the actual value to the positive control (densitometric index). Such methods are well known in the art as described, for example, in Parra et al., *J. Vasc. Surg.* 28:669-675 (1998).

As described herein above, immunoassays including, for example, enzyme-linked immunosorbent assays, radioimmunoassays and quantitative western analysis, can be useful in the diagnostic methods of the invention. Such assays typically rely on one or more antibodies, for example, anti-c-Met antibodies. As used herein, the term "antibody" is used in its broadest sense to include polyclonal and monoclonal antibodies, as well as polypeptide fragments of antibodies that retain binding activity for c-Met of at least about $1 \times 10^5 M^{-1}$. One skilled in the art understands that antibody fragments such as anti-c-Met antibody fragments and including Fab, F(ab')$_2$ and Fv fragments can retain binding activity for c-Met and, thus, are included within the definition of the term antibody as used herein. Methods of preparing monoclonal and polyclonal antibodies are routine in the art, as described, for example, in Harlow and Lane, supra, 1988.

The term antibody, as used herein, also encompasses non-naturally occurring antibodies and fragments containing, at a minimum, one $V_H$ and one $V_L$ domain, such as chimeric antibodies, humanized antibodies and single chain Fv fragments (scFv) that specifically bind c-Met. Such non-naturally occurring antibodies can be constructed using solid phase peptide synthesis, produced recombinantly or obtained, for example, by screening combinatorial libraries consisting of variable heavy chains and variable light chains as described by Borrebaeck (Ed.), *Antibody Engineering* (Second edition) New York: Oxford University Press (1995). A variety of useful anti-c-Met monoclonal and polyclonal antibodies are well known in the art and, in many cases, are commercially available.

The present invention also provides, inter alia, novel methods for diagnosis and prognosis evaluation for cancer.

In one aspect, the amount of soluble c-Met in a biological sample is determined in different patient samples for which either diagnosis or prognosis information is desired, to provide profiles. An profile of a particular sample is essentially a "fingerprint" of the state of the sample. A normal state may be distinguished from a cancerous state, and within cancerous states, different prognosis states (good or poor long term survival prospects, for example) can be determined. Diagnosis may be done or confirmed by comparing patient samples with the known profiles. By assessing the evolution of c-Met levels at different times during disease progression, the stage of disease can be determined as well as the likely prognosis.

A principle of diagnostic testing is the correlation of the results of a procedure with particular clinical parameters. The correlation necessarily involves a comparison between two or more groups distinguished by the clinical parameter. A clinical parameter could be, for example, presence or absence of disease, risk of disease, stage of disease, severity of disease, class of disease or response to treatment of disease. Accordingly, the diagnostician uses this correlation to qualify the status of a subject with respect to the clinical parameter. That is, the diagnostician uses the results of a procedure on a subject to classify or diagnose a subject status with respect to a clinical parameter, the confidence of the diagnosis/classification being related to the classifying or splitting power of the signs or symptoms used in the test.

The methods described herein for quantifying soluble c-met in a biological sample provides information which can be correlated with pathological conditions, predisposition to disease, therapeutic monitoring, risk stratification, among others. Although the data generated from the methods of this invention is suited for manual review and analysis, data processing using high-speed computers can be utilized as well.

The present methods are particularly useful for diagnosing conditions, evaluating whether certain drugs will have a desired effect, and determining prognoses. The present methods can be used for early detection of cancer as well as for the optimization of treatment protocols and analysis of biopsy samples. The present methods can also be used to optimize chemotherapy through assessment of the effect that the chemotherapy has on c-Met levels.

In certain embodiments, the invention provides methods for monitoring the progression of cancer in a patient. The method comprises the steps of providing a first biological sample from the patient, preferably a urine and/or blood plasma sample, measuring the amount of soluble c-Met in the first biological sample at a first time point, providing a second biological sample from the patient, measuring the amount of soluble c-Met in the second biological sample at a second time point, and determining progression of the disease state in the patient based upon the change in the amount of soluble c-Met in the biological sample. In certain embodiments, the amount of soluble c-Met ectodomain in a urine and blood plasma sample will be measured at a first time point and the amount of soluble c-Met ectodomain in a second urine and blood plasma sample will be measured at a second time point and the combined measurement will be used to determine progression of the cancer in the patient. By measuring the amount of c-Met in a patient sample over time, a clinician will be able to determine whether the cancer has, for example, regressed and whether the subject has been effectively treated. A clinician can therefore utilize these measurement for tailoring treatment appropriately. A subject whose cancer has regressed after treatment with an anti-cancer agent will have less detectable c-Met than he did before the treatment. Similarly, a subject whose cancer has remained stable during treatment will have similar levels of c-Met as he did before treatment, and a subject whose cancer has worsened will have increased c-Met levels.

In certain embodiments, the present invention provides methods for measuring the response to cancer therapy comprising the steps of providing a first biological sample, preferably a urine and/or blood plasma sample, measuring the amount of soluble c-Met in the first biological sample at a first time point, providing a second biological sample from the patient, measuring the amount of soluble c-Met in the second biological sample at a second time point, and determining response in the patient based upon the change in the amount of soluble c-Met present in the biological sample. In certain embodiments, the amount of soluble c-Met ectodomain in a urine and blood plasma sample will be measured at a first time point and the amount of soluble c-Met ectodomain in a second urine and blood plasma sample will be measured at a second time point and the combined measurement will be used to determine patient response. The subject may be a positive responder, poor responder, or non-responder. For use herein, a positive responder, is a subject who positively responds to treatment, i.e., a subject who experiences success in amelioration of the cancer, including any objective or subjective parameter such as abatement; remission; diminishing of symptoms or making the condition more tolerable to the patient; slowing in the rate of degeneration or decline; making the final point of degeneration less debilitating; or improving a subject's physical or mental well-being. A positive responder is one in which any toxic or detrimental side effects of the biologically active agent is outweighed in clinical terms by therapeutically beneficial effects. A non-responder is a subject who doesn't respond to the treatment or doesn't respond to a satisfactory level. A poor responder is a subject who responds to treatment but not at the level of the positive responder.

In certain embodiments, the cancer therapy will include the administration of an anti-cancer drug. A clinician or other suitable professional can use the information regarding a subject's likely response level to certain anti-cancer drugs to determine an appropriate treatment regimen for the patient. In certain embodiments, increasing dosages can be provided for those patients that are indicated to be poor responders or non-responders. In certain embodiments, patients that are indicated to be poor responders, or non-responders will receive a different class of drugs or therapy. In certain embodiments, the cancer therapy will be ionizing radiation, hormone ablation therapy, and the like.

Generally, the amount of soluble c-Met ectodomain present in the sample of a patient with premalignant cancer will be less than the amount of soluble c-Met ectodomain present in the sample of a patient with a low grade cancer, and the amount of soluble c-Met ectodomain present in the sample of a patient with a low grade cancer will be less than the amount of soluble c-Met ectodomain present in the sample of a patient with a high grade metastatic cancer.

Anti-cancer drugs are known in the art and include, for example chemotherapeutic agents, alone, or in combination with, radiation treatment, surgical treatment, or treatments using biological or immunomodulatory agents. Chemotherapeutic drugs useful in treating cancer include alkylating agents, antimetabolites, natural products, hormones and antagonists (reviewed in B. A. Chabner and D. L. Longo Eds. Cancer Chemotherapy and Biotherapy, 3rd Edition, 2001). These include, for example, nitrogen mustards, including, for example, mechlorethamine, cyclophosphamide, ifosfamide, melphalan, and chlorambucil; ethylenimines and methylmelamines, including, for example, hexamethylmelamine and thiotepa; alkyl sulfonates, including, for example, busulfan, carmustine, lomustine, semustine, and streptozocin; triazenes, including, for example, dacarbazine and temozolamide, folic acid analogs, including, for example, methotrexate and trimetrexate 5-fluoropyrimidines including, for example, fluorouracil, floxuridine, ftorafur, capecitabine, and eniluracil, cytidine analogs, including cytarabine; 5-azacytidine, gemcitabine, purine analogs and related inhibitors, including, for example, mercaptopurine, thioguanine, fludarabine, cladribine, and pentostatin; vinca alkaloids, including, for example, vinblastine, and vincristine; taxanes including paclitaxel and docetaxel, topoisomerase II inhibitors, including, for example, etoposide, amsacrine and teniposide; topoisomerase I targeting agents including, including, for example, camptothecin, topotecan, irinotecan, and karenitecin, antibiotics, including, for example, dactinomycin, daunorubicin, doxorubicin, bleomycin, plicamycin, and mitomycin; enzymes, including, for example, L-Asparaginase; biological response modifiers, including, for example, IL-2, interferon-alfa IL-1, IL-2, IL-4, IL-12, tumor necrosis factor and macrophage colony stimulating factor, platinum coordination complexes, including, for example, cisplatin, oxaloplatin, and carboplatin; anthracenediones, including, for example, mitoxantrone; thalidomide and derivatives including, for example, revemid, proteosome inhibitors including, for example, bortezomib, substituted ureas, including, for example, hydroxyurea; methylhydrazine derivatives, including, for example, procarbazine; adrenocortical suppressants, including, for example, mitotane and aminoglutethimide; adrenocorticosteroids, including, for example, prednisone; progestins and dexamethasone, including, for example, hydroxyprogesterone caproate, medroxyprogesterone acetate, and megestrol acetate; estrogens, including, for example, diethylstilbestrol and ethinyl estradiol; antiestrogens, including, for example, tamoxifen; androgens, including, for example, testosterone propionate and fluoxymesterone; antiandrogens, including, for example, flutamide; and gonadotropin releasing hormone analogs, including, for example, leuprolide, aromatase inhibitors including, for example, anastrazole (brand name Arimidex®), exemestane (brand name Aromasin®.), and letrozole (brand name Femara®); antibodies directed against cell surface molecules including, for example, rituximab, trastuzumab, CAMPATH, cetuximab and bevacizumab, including antibodies conjugated to toxins, including, for example, gemtuzumab, and antibodies conjugated to radioisotopes including, for example, ibritumomab; anti-cancer antibodies that have been humanized to avoid the development of human antimouse antibodies; small molecule tyrosine kinase inhibitors including, for example, gleevec and iressa (reviewed in Noble et al., Science. 2004; 303:1800-5); faranesyl transferase inhibitors including, for example, R115777 (tipifarnib, Zarnestra®), SCH66336 (lonafarnib, Sarasar®.) and BMS-214662, including formulations of chemotherapy drugs including, for example, liposomal formulations, including arsenic trioxide, including cancer differentiating agents including, for example, all trans retinoic acid, including cancer treatments of any kind that are expected to reduce tumor growth, tumor invasiveness, tumor metastasis or overall tumor burden. Methods of administering chemotherapeutic agents for treating cancer are known in the art. (Goodman and Gilman's The Pharmacological Basis of Therapeutics, Ninth Edition).

The term "cancer therapy" refers to cancer treatment of any kind expected to reduce tumor growth rate, tumor invasiveness, tumor metastasis, or overall tumor burden, including for example, the administration of anti-cancer agents, ionizing radiation therapy, hormone ablation therapy, surgical intervention, and the like.

The invention provides a number of methods, reagents, and compounds that can be used for the diagnosis and prognosis of cancer. It is to be understood that this invention is not limited to particular methods, reagents, compounds, compositions, or biological systems, which can, of course, vary. It is also to be understood that the terminology used herein is for the purpose of describing particular embodiments only, and is not intended to be limiting. As used in this specification and the appended claims, the singular forms "a", "an", and "the" include plural referents unless the content clearly dictates otherwise.

About" as used herein when referring to a measurable value such as an amount, a temporal duration, and the like, is meant to encompass variations of ±20% or ±10%, more preferably ±5% even more preferably ±1%, and still more preferably ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein.

EXAMPLES

Reagents and Cell Culture

Full length purified recombinant human hepatocyte growth factor (HGF) protein was obtained from R&D Systems (294-HG, Minneapolis, Minn.). Antibodies against c-Met were obtained from R&D Systems (Minneapolis, Minn.) or Upstate Biotechnology (DO-24 anti-c-Met mAb; Lake Placid, N.Y.) as noted below.

The following human normal/tumor and primary tumor/metastasis cell line pairs derived from single individuals were obtained from ATCC and maintained according to ATCC recommendations: CRL7636 (normal skin) and CRL7637 (skin melanoma), HTB125 (normal mammary gland) and HTB126 (mammary gland ductal carcinoma), and CCL228 (colorectal adenocarcinoma) and CCL227 (lymph node metastasis of colorectal adenocarcinoma). The human cell line pair UOK124 (renal cell carcinoma) and UOK124 LN (lymph node metastasis of renal cell carcinoma), as well as UOK261 (bladder cancer) were developed at the Urologic Oncology Branch, National Cancer Institute, National Institutes of Health, Bethesda, Md. 20892 USA; Athauda et al., *Clin. Cancer Res.* 12: 4154-4162, 2006). UOK124, UOK124 LN, UOK261, A431 (epidermoid carcinoma), U-87 MG (glioblastoma), C100 (breast carcinoma), H1.177 (C100 transfected with Nm23), PC3 (prostate carcinoma), PC3M (PC3 derived metastatic variant) and PC3M M×A (PC3M transfected with M×A) cells were maintained in DMEM supplemented with 10% fetal bovine serum, antibiotics and antimycotics. B5/589 human mammary epithelial cells were cultured as previously described (Stahl et al., *Biochem J* 1997; 326:763-72). The MCF-10A derived breast epithelial cell lines 141-M4 (MCF-10A or M1, MCF10AT1k.cl2 or M2, MCF-10CA1h or M3 and MCF-10CA1a.cl1 or M4) (Santner et al., *Breast Cancer Res Treat* 2001; 65:101-10) were obtained from the Barbara Ann Karmanos Cancer Institute (Detroit, Mich.) and were maintained in DMEM/F-12 supplemented with 5% horse serum, 0.029M sodium bicarbonate, 10 mM HEPES, penicillin and streptomycin at 37° C. 5% $CO_2$. This culture medium was supplemented with 10 μg/ml insulin, 20 ng/ml EGF, 0.5 μg/ml hydrocortisone and 100 ng/ml cholera toxin for the M1 and M2 cell lines.

SDS-PAGE and Immunoblotting

Analysis of cellular and soluble c-Met by immunoprecipitation and immunoblotting was performed as described previously (Stahl et al., *Biochem J* 1997; 326:763-72). Samples for soluble c-Met analysis were obtained by harvesting conditioned media (cell culture supernatants) prior to detergent extraction; conditioned media was subjected to high speed centrifugation and 0.2 micron filtration to remove cells and debris. To obtain cellular c-Met samples, intact cells were serum deprived for 16 or 24 h as noted, lysed in cold buffer containing non-ionic detergents and protease and phosphatase inhibitors and cleared by high speed centrifugation. After immunoprecipitation of clarified detergent extracts for 2 h on ice, immunocomplexes were captured using immobilized protein-G (GammaBind G-Agarose, Pharmacia), washed, eluted with SDS sample buffer and subjected to SDS-PAGE and electrophoretic transfer to PVDF membranes (Immobilon P, Millipore). Immunodetection was performed by conventional methods using enhanced chemiluminescence (ECL Plus, Amersham).

Electrochemiluminescence Immunoassays

Streptavidin coated 96-well plates designed specifically for use in a Meso Scale Discovery (MSD) Sector 2400 Imager were first blocked with I-Block solution (300 μl/well, 1 h; Applied Biosystems catalog #A1300) that had been prepared according to the manufacturers instructions. Wells were then washed 3 times with PBS (150 μl/well).

For c-Met ectodomain assays, a biotin-tagged, affinity purified c-Met ectodomain specific capture antibody (R&D BAF 358 diluted in 0.5% BSA in PBS) was added to each well (5 ug/ml, 25 μl/well) for 1 h with shaking. Wells were washed 3 times with PBS before adding samples or standards (R&D 358-MT recombinant c-Met ectodomain-IgG-Fc fusion protein in PBS+0.5% BSA). Standards (100 μl/well) were added to generate a curve from 0.01 ng/ml to 100 ng/ml in semi-log increments for 1 h with shaking. Samples for soluble c-Met analysis were obtained by harvesting conditioned media (cell culture supernatants) prior to detergent extraction; conditioned media was subjected to high speed centrifugation and 0.22 micron filtration to remove cells and debris, then stored at −80° C. prior to c-Met quantitation. In some cases conditioned media was concentrated using Centricon YM-10 microconcentration units (Millipore, Inc.) prior to analysis, as described in the text, or subjected to a single round of immunodepletion using the human c-Met ectodomain specific monoclonal antibody DO24 (Upstate Biotechnology) followed by antibody capture with protein G agarose. Wells were washed 3 times with PBS before adding detection antibody (R&D AF 276 labeled with MSD Sulfotag diluted in 0.5% BSA in PBS) at 1 ug/ml, 25 μl/well for 1 h with shaking. Wells were then washed 4 times with PBS before adding MSD Read Buffer T with surfactant (150 μl/well) and then read immediately in a MSD Sector 2400 Imager.

For cellular c-Met assays, intact cells at 80% confluence were serum deprived for 24 h, washed twice with cold PBS and then lysed in cold buffer containing non-ionic detergents and protease and phosphatase inhibitors. Detergent extracts were clarified by high speed centrifugation and applied to 96-well plates as described for soluble c-Met ectodomain samples, above.

c-Met assays can be performed on biological sample, e.g., biological tissue or biological fluid from a patient or human patient. The biological tissue can be assayed for c-Met ectodomain as a detergent extract of the tissue. Biological tissue from a patient can be extracted with non-ionic detergent buffer solutions as described herein for preparing cell extracts. The tissue can be minced or ground (at 4° C. or on ice) to maximize surface area available for extraction, and generally the extraction (also on ice) is performed for a much longer period (2-3 hours) as opposed to a few minutes for cultured cells. See, for example, U.S. Pat. No. 5,674,753.

For HGF immunoassays, I-Block treated plates were coated as described above with an affinity purified HGF specific capture antibody (R&D MAB 694 diluted in 0.5% BSA in PBS) that had been biotin labeled. Wells were washed as described above before adding samples or standards (R&D 294-HG recombinant HGF protein in PBS+0.5% BSA); standards were added to generate a curve from 0.03 ng/ml to 30 ng/ml in semi-log increments. Wells were washed before adding detection antibody (R&D AF-294 labeled with MSD Sulfotag diluted in 0.5% BSA in PBS) at 1 ug/ml, 25 μl/well. Wells were then washed 4 times with PBS before adding Read Buffer T and reading in a MSD Sector 2400 Imager.

All samples were measured in quadruplicate unless otherwise noted. Mean values from negative control wells were subtracted from all other raw values and a standard curve was then constructed by plotting signal intensity against 358-MT c-Met Fc fusion protein or recombinant HGF protein standard concentration. A non-linear regression curve fitting algorithm (Microsoft Excel or GraphPad Prism software) was used to generate an equation from which sample values for c-Met or HGF concentration were derived from mean signal intensity values. Mean values among groups were compared for statistically significant differences using unpaired t-test (paired human cell lines) or analysis of variance (ANOVA; MCF10A derived cell lines); $R^2$ and P values are presented in the text and figure legends.

Human Tumor Xenografts in Mice

Figure 6:
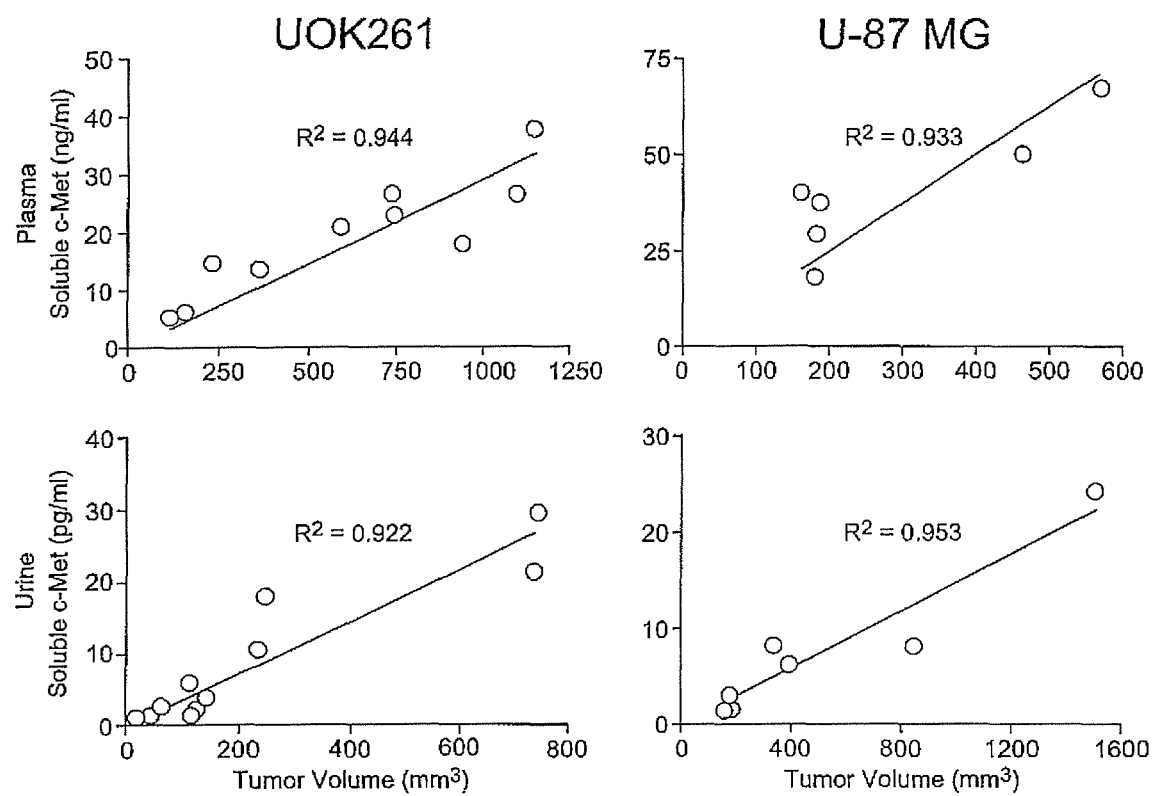
FIG. 6. c-Met shedding in mice bearing human tumor cell xenografts. Soluble human c-Met concentrations in plasma (ng/ml, upper panels) or urine samples (pg/ml, lower panels) obtained from mice bearing subcutaneous UOK261 human bladder carcinoma (left panels) or U-87 MG human glioblastoma (right panels) cell xenografts plotted against the corresponding tumor volume ($mm^3$) in each mouse at the time of sample procurement. Values represent the mean of triplicate measurements; standard deviations are smaller than the symbol size. Each line and corresponding $R^2$ value represent a best fit linear regression analysis forced through the origin and were performed using GraphPad Prism software.

Subconfluent UOK261 and U-87 MG cells were trypsinized, washed two times in PBS to remove serum and then resuspended in HBSS at a concentration of $1 \times 10^7$ cells/ml. One hundred microliters containing $1 \times 10^6$ cells were injected subcutaneously into the right flank of 12-week-old male SCID/beige mice (Taconic Inc., Germantown, N.Y.). Tumor growth was monitored weekly by caliper measurements and tumor volume was calculated based on the formula (length.times.length.times.width)/6. Blood was obtained via the tail vein or retromandibular perforation; samples were collected in the presence of citrate as an anticoagulant were centrifuged at 1500 rpm, 4° C. to remove cells and plasma samples were stored at −80° C. prior to analysis. At each of three weekly time points 4 mice were sampled per group. Samples were analyzed for soluble c-Met using the electrochemiluminescence immunoassay described above; values shown represent the mean of triplicate measurements. In FIG. 6, standard deviations are smaller than the symbol size in all cases. Mouse urine sample pH was adjusted to pH 7.5 with Trizma-HCl, 2M, pH 8.0 (Sigma), then centrifuged at 1500 rpm for 5 minutes to remove cells and debris. Pooled SCID/beige normal mouse plasma was used as a diluent for standard curves and was obtained in bulk from Taconic Inc. Pooled urine from normal SCID/beige mice was pH-corrected and used as a diluent for standard curves run in assays to measure c-Met concentration in mouse urine samples. $R^2$ and P values from linear regression analysis of mouse data are presented in the text and figure legends.

c-Met Shedding by Cultured Cells: Characterization and Assay Development c-Met ectodomain shedding was examined in a cultured cell model of breast cancer progression where successive derivatives of the parent cell line show increasing malignancy (Santner et al., *Breast Cancer Res Treat* 2001; 65:101-10). MCF-10A (M1) is a spontaneously immortalized normal breast epithelial cell line which was transfected with activated Hras and xenografted in mice to obtain the premalignant MCF10AT1k.cl2 (M2) cell line. Subsequent passages in mice and single cell cloning facilitated the isolation of cell lines that produced tumors with the phenotypic characteristics a low grade carcinoma (MCF-10CA1h or M3) and a high grade metastatic carcinoma (MCF-10CA1a.cl1 or M4). In contrast to many carcinoma derived cell lines where c-Met is overexpressed, cell surface c-Met expression among the four cultured cell lines appeared to decrease with increasingly malignant phenotype (FIG. 1A). Nonetheless, analysis of c-Met shedding over 16 h by immunoblotting with ectodomain-specific monoclonal antibodies showed progressively higher ectodomain levels from normal cells to those displaying a metastatic phenotype (FIG. 1B). c-Met ectodomain fragments of approximate molecular masses 75, 85 and 100 kDa were the predominant species observed, similar to those observed in the normal human mammary epithelial cell line B5/589 (FIG. 1B) and to the predominant species present in cell culture supernatants and human plasma as reported previously [3-7]. These c-Met reactive protein bands were detectable with several antibodies against the c-Met ectodomain, but not with polyclonal antisera raised against a peptide corresponding to the carboxyl terminal c-Met sequence (data not shown).

Figure 2:
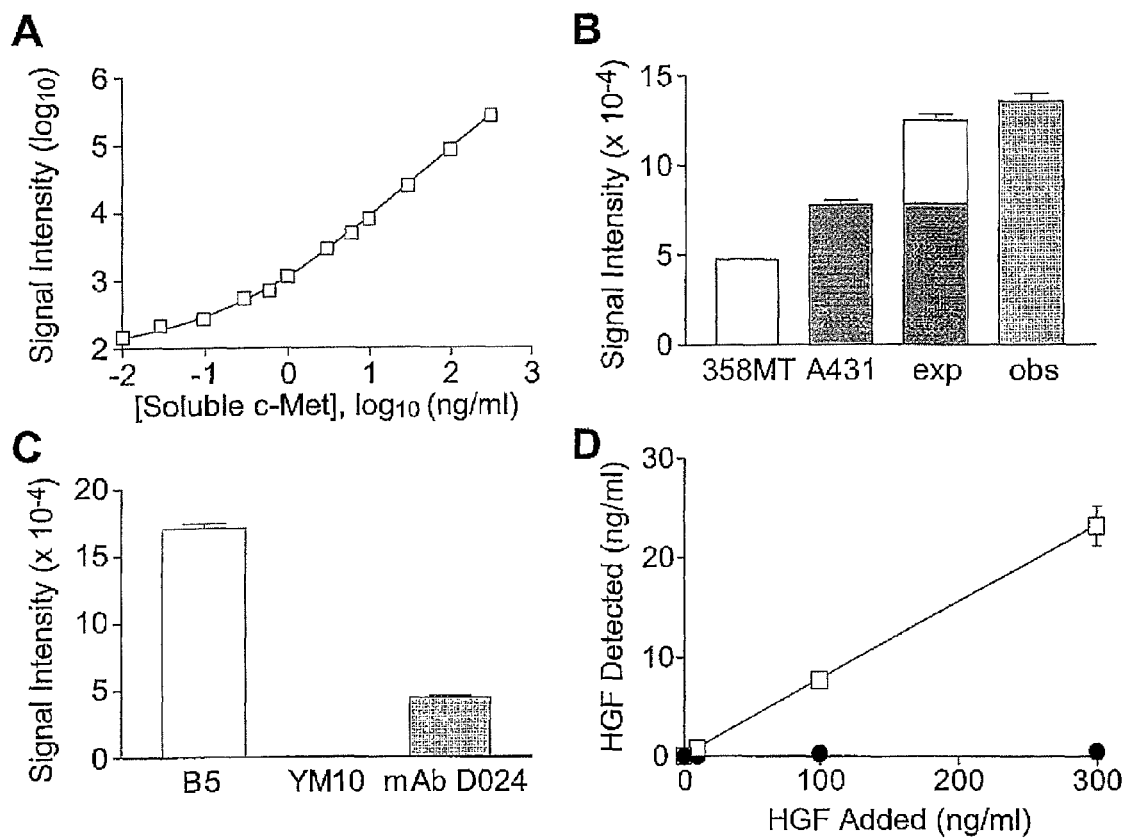
FIG. 2. Quantitation of c-Met shedding using an electrochemiluminescent two site immunoassay. 2A. Standard curve of purified recombinant c-Met ectodomain-IgG fusion protein (358-MT). Mean values from quadruplicate samples are shown as log [soluble c-Met] in ng/ml vs. log [signal intensity] in relative units. Standard deviations are smaller than the symbol size. 2B. Analysis of sample quenching in a431 human epidermoid carcinoma cells. Cells were serum deprived for 24 h and soluble c-Met ectodomain was measured in the presence and absence of added 358-MT. Mean values of quadruplicate samples from 358-MT (358MT, open bar), A431 conditioned medium (A431, dark gray bar), and A431 conditioned medium+358-MT (obs, light gray bar) are shown+/−standard deviation. The expected sum of 358-MT and A431 conditioned medium sample signals is also shown (exp, dark-gray/open bar). 2C. Soluble c-Met in 24 h B5/589 conditioned media (B5, open bar) was filtered using a 10 kDa cutoff molecular sieve and soluble c-Met in the filtrate was measured (YM10, dark gray bar). 24 h B5/589 conditioned medium (open bar) was immunodepleted using an ectodomain-specific monoclonal antibody (mAb DO24, Upstate Biotechnology; light gray bar). 2D. HGF binding (ng/ml) was measured in samples containing equivalent amounts of a c-Met Fc fusion protein (open squares) and c-Met ectodomain present in B5/589 conditioned medium (black circles), as a function of the concentration of HGF added (ng/ml). Error bars represent standard deviation; where no bars are seen, the deviation is smaller than the symbol size.

To better characterize c-Met shedding across a range of cell lines and biological samples, a two site immunoassay was developed to provide greater sensitivity, higher throughput and more precise quantitation than immunoblotting. Distinct human c-Met specific antibodies are used for capture and detection; capture antibodies were biotin labeled for use with streptavidin coated multiwell plates and the amount of detection antibody bound was measured by electrochemiluminescence generated using ruthenium chelates in the presence of sacrificial redox co-reactants. The optimized c-Met immunoassay has a threshold of detection of 750 fg for the purified recombinant c-Met ectodomain protein and a dynamic range of four log units (FIG. 2A). Sample quenching or hypersensitivity that could occur in complex biological samples was investigated by adding known amounts of recombinant c-Met ectodomain to cultured cell supernatants from B5/589 mammary epithelial cells (data not shown) or A431 epidermoid carcinoma cells (FIG. 2B), both of which contained shed c-Met ectodomain as determined by immunoblotting. Agreement between expected and observed c-Met concentrations indicated the absence of any interference (FIG. 2B). Ultrafiltration of B5/589 conditioned medium through a membrane with a 10 kDa cutoff removed all of the c-Met signal, consistent with the ectodomain molecular masses observed by immunoblotting (FIG. 2C). The c-Met selectivity of the immunoassay was tested by subjecting B5/589 conditioned medium to immunodepletion using a monoclonal antibody against c-Met ectodomain (DO-24) that was distinct from either capture or detection antibody used in the immunoassay. As shown in FIG. 2C, a single round of immunodepletion resulted in an 80% loss of signal.

To determine whether shed c-Met ectodomain fragments could act as competitive antagonists of ligand binding by cell surface receptors, the two site c-Met immunoassay was adapted to analyze the HGF binding capacity of c-Met fragments cultured cells conditioned medium. A purified recombinant full length c-Met ectodomain-IgG Fc fusion protein was used as positive control for HGF binding. The amount of c-Met ectodomain present in B5/589 conditioned medium was determined from a c-Met-Fc standard curve and assays were designed such that equal amounts of c-Met ectodomain in B5/589 conditioned medium and in the c-Met Fc fusion protein preparation were captured in replicate wells. Purified recombinant HGF was added to two sets of wells at concentrations of 10, 100 and 300 ng/ml; one set of wells was then detected using anti-c-Met and the other with anti-HGF. An HGF standard curve was created using the same HGF detection antibody and an HGF-specific capture antibody. No change in c-Met detection was observed in c-Met Fc containing wells that had bound HGF, indicating that bound HGF did not interfere with c-Met capture or detection (data not shown). As shown in FIG. 2D, the c-Met Fc fusion protein bound HGF in direct proportion to the amount added, whereas no HGF binding was detected for the c-Met fragment present in B5/589 conditioned medium. These results, consistent with prior studies (Wajih et al., *Circ Res* 2002; 90:46-52), show that the predominant c-Met ectodomain fragments found in B5/589 cell culture supernatants have lost meaningful HGF binding capability. In light of the observation that the B5/589 c-Met ectodomain fragments are very similar in size and distribution to those shed by a variety of cultured cell lines as well as to what has been found in human plasma (Wajih et al., *Circ Res* 2002; 90:46-52), c-Met shedding does not yield a soluble receptor fragment that could compete efficiently for ligand binding by intact cellular c-Met.

c-Met Shedding Correlates with Malignancy in Cultured Cell Cancer Models

Figure 3:
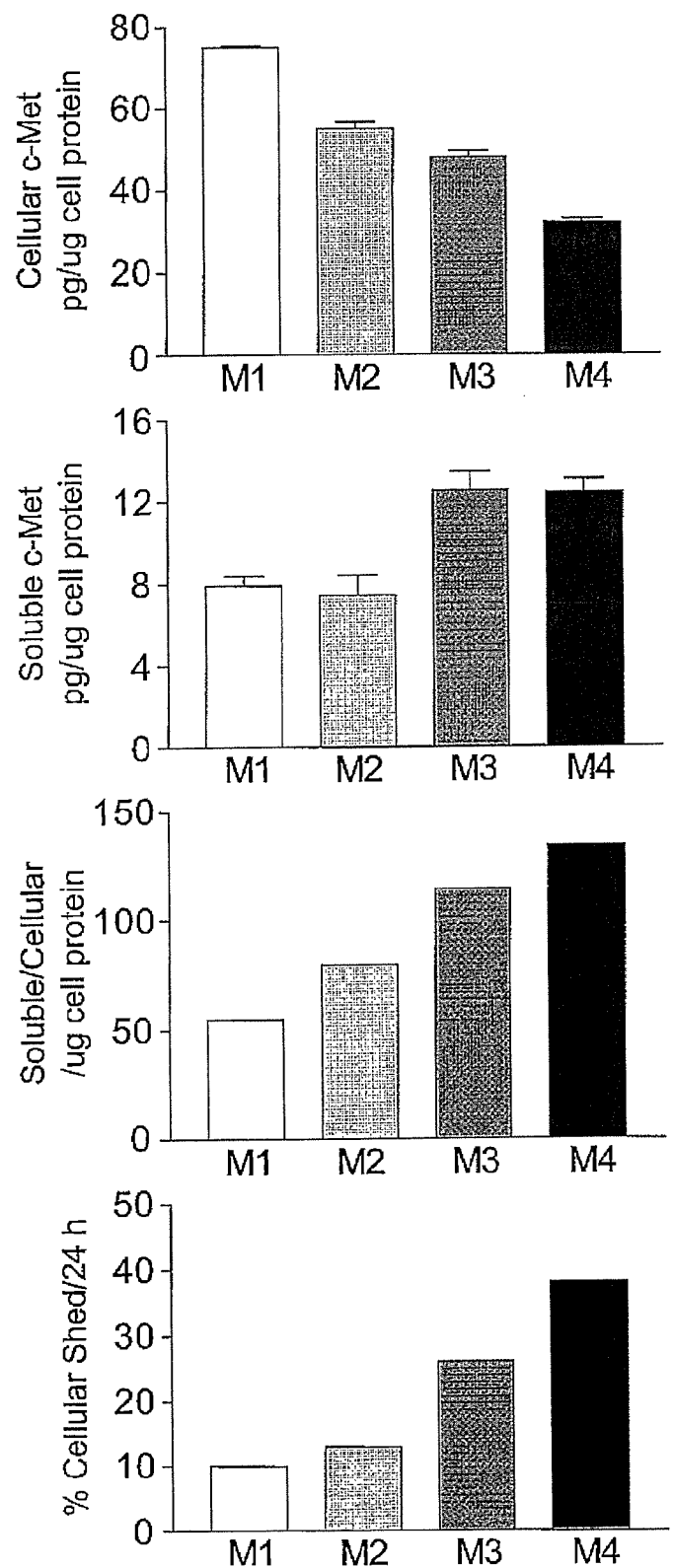
FIG. 3. Quantitation of c-Met expression and shedding in a cultured cell model of breast tumor progression. Cell surface and soluble c-Met levels were measured in the MCF10A derived cell lines M1 (open bars), M2 (light gray bars), M3 (dark gray bars) and M4 (black bars). Non-ionic detergent extractable c-Met is expressed as pg/ug cell protein (Cellular c-Met, top panel); c-Met ectodomain present in 24 h cell conditioned medium is shown expressed as pg/ug cell protein (Soluble c-Met, $2^{nd}$ panel) and after normalization to detergent extractable c-Met (Soluble/Cellular, $3^{rd}$ panel). The percentage of detergent extractable c-Met that became soluble in 24 h is shown in the bottom panel.

Quantitative analysis of c-Met shedding by the MCF 10A derived breast cancer cell lines that were analyzed previously by immunoblotting showed excellent agreement in the trends among the cell lines for both cellular c-Met expression and c-Met ectodomain shedding (FIG. 1B and FIG. 3, upper panels). The external recombinant protein standard in the immunoassay allows results to be expressed in absolute terms, e.g. receptor concentration or number per total cellular protein or per cell. This enables realistic comparisons between successive experiments, different cell lines or with other biological samples. Manipulation of the numerical results also offers insight into trends in shedding relevant to molecular mechanism, such as determining shedding rate per cellular receptor (FIG. 3, $3^{rd}$ panel) or the percentage of cellular receptor shed per time interval (FIG. 3, bottom panel). In the MCF10A derived model of breast cancer progression, the steady state cellular c-Met expression level is progressively and significantly lower at each step of increasingly malignant phenotype (ANOVA $R2=0.998$; $P<0.0001$). In contrast, c-Met shedding is significantly increased with the change from premalignant (M2) to malignant (M3) phenotype (FIG. 3, $2^{nd}$ panel, t-test P<0.001). This trend is maintained in the metastatic (M4) cell line (FIG. 3, $2^{nd}$ and $3^{rd}$ panels) and shedding in M4 is nearly four-fold higher than its normal counterpart M1 when expressed as a function of available cellular c-Met (FIG. 3, bottom panel; 4 group ANOVA $R^2 > 0.995$; P<0.0001). The observed trends in expression and shedding are consistent with significant and progressive increases in proteolytic activity characteristic of advancing breast cancer.

Cellular and soluble c-Met levels in a series of paired human cell lines, each obtained from a single cancer patient, derived from tumor vs. corresponding normal tissue or, primary tumor vs. distant metastatic lesion were measured. Specifically, the paired cell lines were derived from normal skin (CRL7636) and skin melanoma, (CRL7637), normal mammary gland (HTB125) and mammary gland ductal carcinoma (HTB126), colorectal adenocarcinoma (CCL228) and lymph node metastasis of colorectal adenocarcinoma (CCL227), and renal cell carcinoma (UOK124) and lymph node metastasis of renal cell carcinoma (UOK124 LN).

Figure 4:
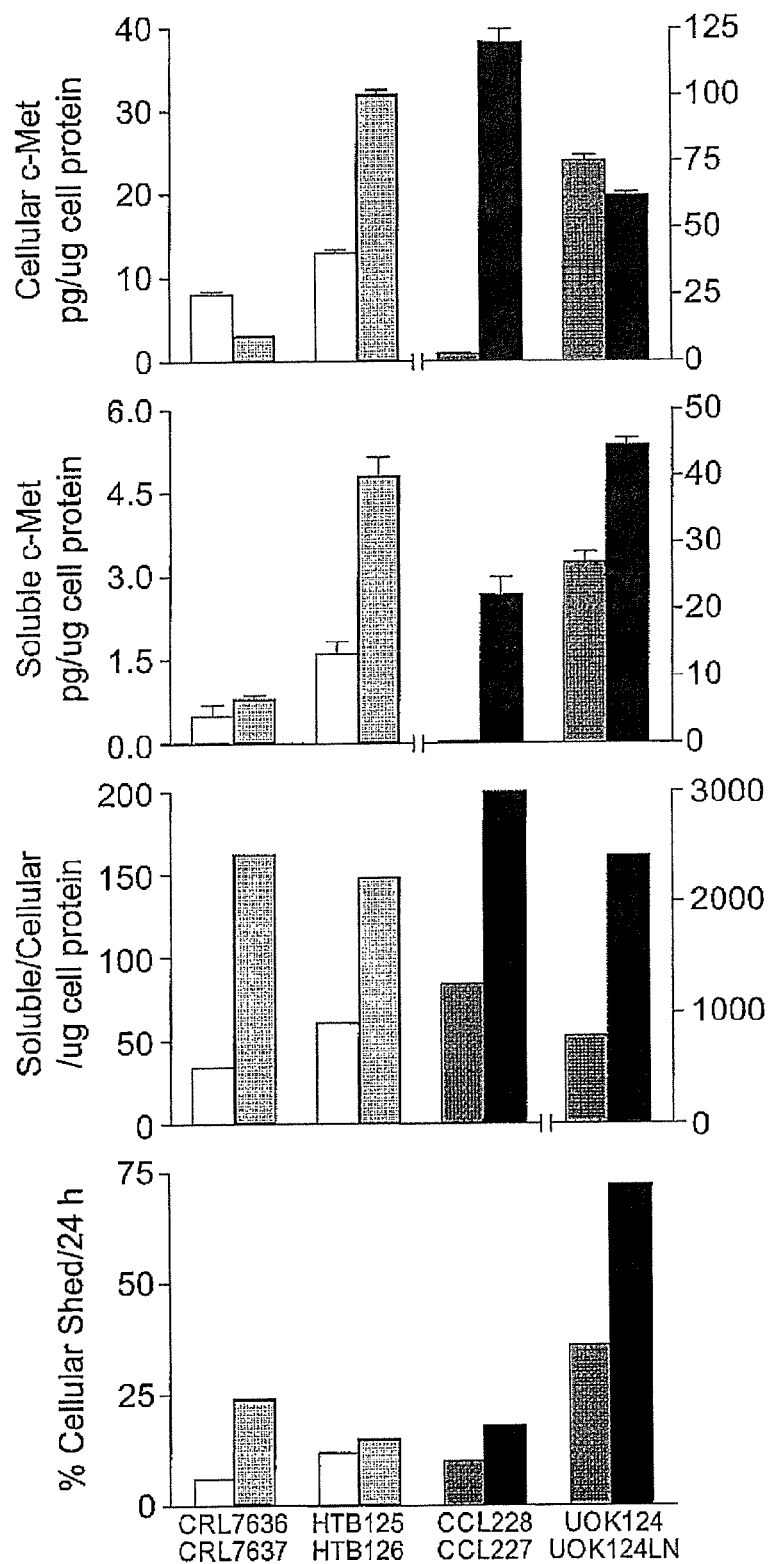
FIG. 4. Quantitation of c-Met expression and shedding in paired cell line models of cancer progression. Cell line pairs, each derived from a single patient, were compared for levels of cellular (top panel) and soluble ($2^{nd}$ panel) c-Met. These data were used to calculate the amount of soluble receptor shed after 24 h corrected for cellular receptor ($3^{rd}$ panel) and the amount of soluble receptor produced in 24 h as a percentage of cellular receptor (bottom panel). Cell lines derived from normal tissue (open bars) corresponding to the tissue of tumor origin were paired with tumor-derived cell lines (light gray bars) and other tumor derived cell lines (dark gray bars) were paired with cell lines derived from corresponding metastatic lesions (black bars). CRL7636 is a normal skin cell line; CRL7637 is a skin melanoma cell line; HTB125 is a normal mammary gland cell line; HTB126 is a mammary gland ductal carcinoma cell line; CCL228 is a colorectal adenocarcinoma cell line; CCL227 is a lymph node metastasis of colorectal adenocarcinoma cell line; UOK124 is a renal cell carcinoma cell line; and UOK124 LN is a lymph node metastasis of renal cell carcinoma cell line.

All four cell line pairs exhibited one overall trend similar to that displayed by the MCF10A model: significantly greater c-Met shedding rate with more malignant phenotype FIG. 4, $2^{nd}$, $3^{rd}$ and $4^{th}$ panels). In contrast, cellular c-Met levels varied widely among the paired lines (FIG. 4, top panel). Relative to the normal skin derived cell line CRL7636, cellular c-Met was 60% lower then in the paired melanoma derived cell line CRL7637 (top panel), while soluble c-Met concentration was 60% greater ($2^{nd}$ panel), contributing to a 4-fold greater c-Met shedding rate per cell protein ($3^{rd}$ panel) and per receptor ($4^{th}$ panel) correlating with the acquisition of malignancy. These findings suggest that, similar to the MCF10A derived cell lines, significantly increased proteolytic activity was the primary cause of the observed trend. In contrast, in the cell line pair derived from normal mammary gland and ductal carcinoma (HTB125 and HTB126), acquisition of malignancy correlated with 2.5 fold greater cellular c-Met level (top panel) and 4-fold greater soluble c-Met level ($2^{nd}$ panel) producing a 2.5 fold greater c-Met shedding rate per cell protein ($3^{rd}$ panel). This trend represented only a modest increase in the percentage of cellular c-Met shed in 24 h (bottom panel), suggesting that unlike the MCF10A derived breast cancer model, receptor overexpression contributed significantly to the increased receptor shedding observed with malignant transformation. This difference in underlying mechanism of increased c-Met shedding between two breast cancer cell models could reflect the oncogenic heterogeneity in breast cancer that is becoming more broadly appreciated.

Similar in trend to HTB125 and HTB126, but remarkable in magnitude, the cell line derived from a lymph node metastasis of colorectal carcinoma (CCL227) showed 40-fold greater cellular c-Met expression relative to the primary tumor derived cell line (CCL228) and 75-fold greater rate of c-Met shedding per total cell protein (FIG. 4, upper two panels). Correcting these values for receptor protein yielded a 2.7 fold greater shedding rate in the metastasis-derived line relative to the primary tumor line (FIG. 4, $3^{rd}$ panel). The renal cell carcinoma derived cell line UOK124 and corresponding lymph node metastasis derived line UOK124 LN showed little difference in cellular c-Met expression (top panel), while soluble c-Met level was 60% greater in UOK124 LN (2nd panel), contributing to a 3-fold greater c-Met shedding rate per cellular receptor ($3^{rd}$ panel) and a doubling of the percentage of cellular receptor shed in 24 h (bottom panel). Thus, similar to the trends observed for the MCF10A derived breast carcinoma model and the skin melanoma cell line pair, significantly greater proteolytic activity was likely to be responsible for the greater c-Met shedding rate that correlated with increased malignancy.

Figure 5:
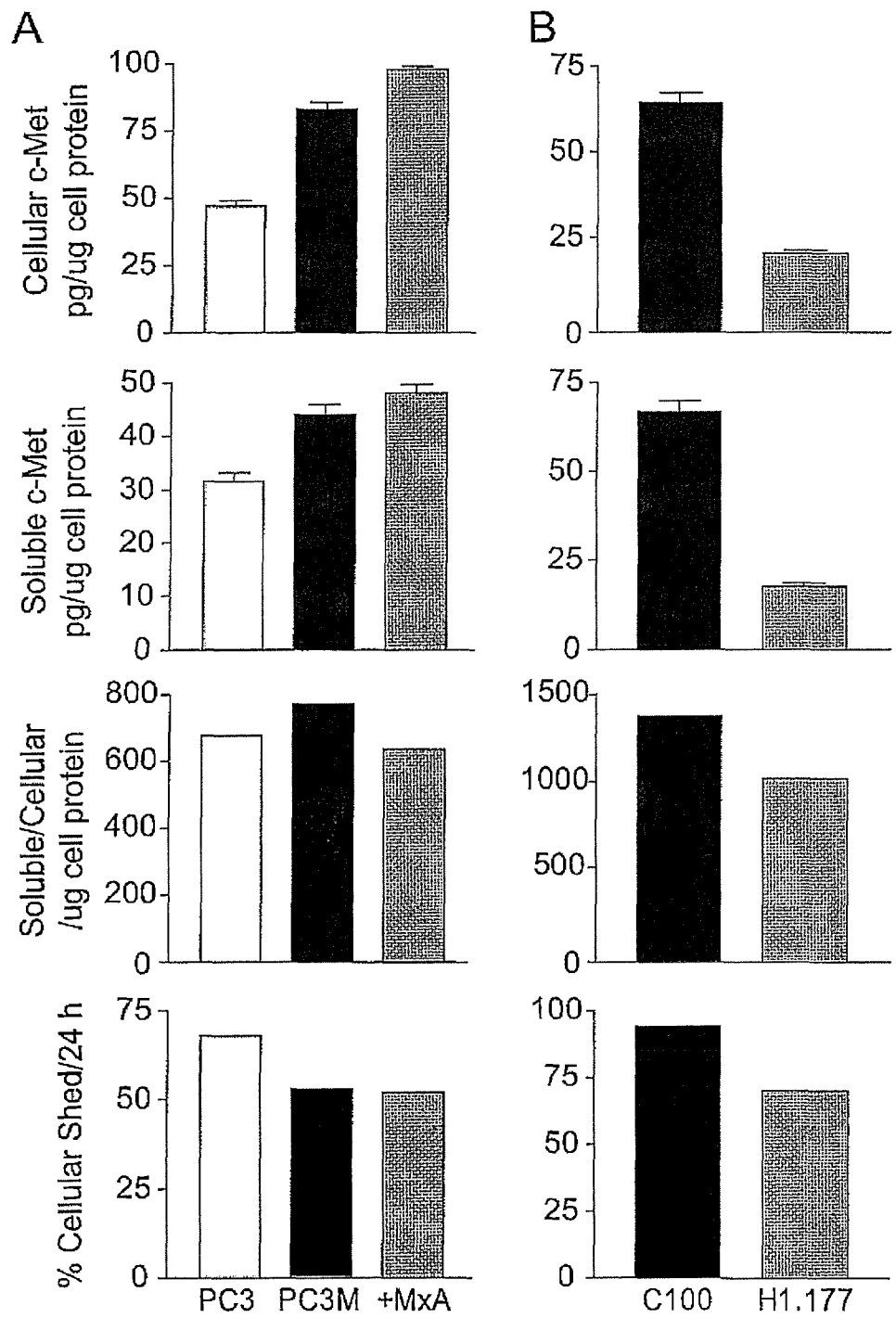
FIG. 5. Genetically modified cultured cell models of cancer progression. 5A. The human prostate cancer derived cell line PC3 (open bars), a derived metastatic variant PC3M (black bars) and PC3M transfected with an ADxA gene expression plasmid (+MxA, gray bars) were compared for levels of cellular (top panel) and soluble ($2^{nd}$ panel) c-Met. These data were used to calculate the amount of soluble receptor shed after 24 h corrected for cellular receptor ($3^{rd}$ panel) and the amount of soluble receptor produced in 24 h as a percentage of cellular receptor (bottom panel). 5B. The human breast cancer derived cell line C100 (black bars) and a C100 derivative cell line cloned after transfection with an NM23 gene expression plasmid (H1.177, gray bars) were compared for levels of cellular and soluble c-Met as in Panel A.

In addition to cultured normal/tumor or tumor/metastasis cell line pairs, cellular and soluble c-Met levels in two genetically engineered models representing reconstitution of metastasis suppressor genes in aggressively malignant prostate and breast tumor derived cell lines were examined. The prostate cancer cell line PC3 is tumorigenic in mice but not metastatic; PC3M is a PC3 derived cell line that is aggressively tumorigenic and metastatic (Chu et al., *Cancer Genet Cytogenet* 2001; 127:161-7.) This phenotypic difference was exploited to identify genes whose loss could contribute to metastasis in prostate cancer, leading to the identification of the M×A gene as a suppressor of metastasis (Aebi et al., *Mol Cell Biol* 1989; 9:5062-72 and unpublished observations). Upon reconstitution of M×A expression in PC3M, the aggressive metastatic phenotype of cultured cell xenografts in mice is reverted to that of the parental cell line (unpublished observations). Cellular c-Met expression in PC3M was nearly double that of PC3; restoration of M×A expression was associated with an even greater cellular c-Met expression level (FIG. 5A, top panel). Shedding by PC3M was 50% greater than that of the parental cell line, consistent with the overall trend of increased shedding with increasing malignancy observed in other cell models (FIG. 5A, $2^{nd}$ panel), and apparently driven by increased c-Met expression. While the absolute level of c-Met shedding in PC3M and PC3M M×A transfectants was similar, a lower rate of c-Met shedding per cellular receptor was detected in M×A transfectants (FIG. 5A, $3^{rd}$ and $4^{th}$ panels). These results suggest that M×A expression had no significant effect on c-Met expression, but suppressed the shedding mechanism to a level comparable to that displayed by the non-metastatic PC3 cell line.

In contrast to the PC3 based model of prostate cancer metastasis, a dramatic effect on cellular c-Met expression was exhibited by the metastasis suppressor gene Nm23 in a genetically engineered cell model of breast cancer progression (FIG. 5B). In this model, the breast cancer cell line C100, which aggressively forms primary tumors and metastases in mouse xenografts, was reverted to a non-metastatic phenotype upon transfection with Nm23 (H1.177) (Leone et al., Oncogene 1993; 8:2325-33]. Correlated with the loss of metastatic phenotype was 70% lower cellular c-Met expression in H1.177 relative to the parental cell line (FIG. 5B, top panel) and 75% lower soluble c-Met production (FIG. 5B, $2^{nd}$ panel). A 20% lower level of c-Met shedding per cellular receptor was also associated with Nm23 expression (FIG. 5B, $3^{rd}$ and $4^{th}$ panels), suggesting that shedding was attenuated primarily through the suppression of c-Met expression by Nm23.

c-Met Shedding Correlates with Tumor Burden in Tumor Xenograft Mouse Models

It was observed that cultured tumor cells expressing c-Met tended to shed more c-Met ectodomain than their normal tissue counterparts, independent of changes in overall c-Met expression level, and that this tendency was enhanced with increasingly malignant phenotype. Two different human tumor cell lines were injected subcutaneously with known c-Met shedding rates (data not shown) into immunocompromised (SCID/Beige) mice and thereafter measured tumor volume and plasma soluble c-Met levels at weekly intervals. The cell line UOK261 was derived from a human bladder carcinoma and displayed a relatively high level of soluble c-Met in culture, whereas the cell line U-87 MG was derived from a human glioblastoma and displayed a lower level of c-Met shedding in culture. c-Met signaling is suspected of playing an important role in the progression of both cancers represented by these models [Burgess et al., *Cancer Res* 2006; 66: In Press; Rosen et al., *J Urol* 1997; 157:72-8; Cheng et al., *J Clin Oncol* 2002; 20:1544-50.) Note that the antibodies used in the immunoassay described here do not cross-react with mouse c-Met, thus the assay was conducted in the absence of any normal soluble murine c-Met background; any c-Met detected originated from the human tumor xenografts. Pooled plasma samples obtained from the same strain of mice was used as a diluent for the recombinant c-Met ectodomain-Fc standard curve, so that the absolute soluble c-Met values obtained could be related directly to those obtained from cultured cell experiments, as well as to future animal studies.

Remarkably, soluble human c-Met was easily detected in plasma samples obtained from several mice receiving UOK261 xenografts more than a week before subcutaneous tumors became palpable (data not shown). Non-palpable tumors up 5.0 mm$^3$ in volume are difficult to detect radiologically and represent an early but nonetheless clinically relevant stage of tumorigenesis. The soluble c-Met fragments measured in the immunoassay were similar in size to the fragments found in cultured cell conditioned media, as determined by SDS-PAGE and immunoblotting (data not shown). With increasing tumor mass, each mouse showed significant weekly increases in plasma c-Met levels ($P<0.05$; data not shown); these data were pooled and plotted as plasma c-Met against tumor volume (FIG. 6, left upper panel). Regression analysis demonstrated a direct linear relationship between circulating soluble c-Met concentration and tumor burden (FIG. 6, left upper panel, $R^2=0.944$; n=4 animals). Consistent with the lower level of c-Met shedding by cultured U-87 MG cells, soluble c-Met was not detected in plasma samples from mice receiving the U-87 MG glioblastoma xenografts before the tumors became palpable. Nonetheless, the smallest measurable tumors were each associated with plasma c-Met levels that were well above the threshold of detection, and each mouse showed significantly increasing c-Met concentrations measured at weekly intervals ($P<0.05$; data not shown). Regression analysis of the pooled data plotted as c-Met concentration against tumor volume also supported a direct linear soluble c-Met/tumor burden relationship (FIG. 6, right upper panel, $R^2=0.933$; n=4 animals).

As shown in the left lower panel of FIG. 6, subcutaneous UOK261 xenografts produced urinary soluble c-Met concentrations that were detectable at very small tumor sizes and that increased linearly with tumor burden over weekly intervals ($R^2=0.922$, $P<0.01$, n=4 animals). Urinary soluble c-Met concentrations were typically less that $\frac{1}{1000}^{th}$ of corresponding plasma c-Met concentrations (FIG. 6, left lower panel). Urine samples from mice receiving U-87 MG xenografts also contained soluble c-Met at early stages of tumor growth that increased significantly with time in each mouse ($P<0.05$; data not shown), and group data showed a similar direct linear relationship between c-Met concentration and overall tumor burden (FIG. 6, right lower panel; $R^2=0.953$, n=4 animals).

Figure 7:
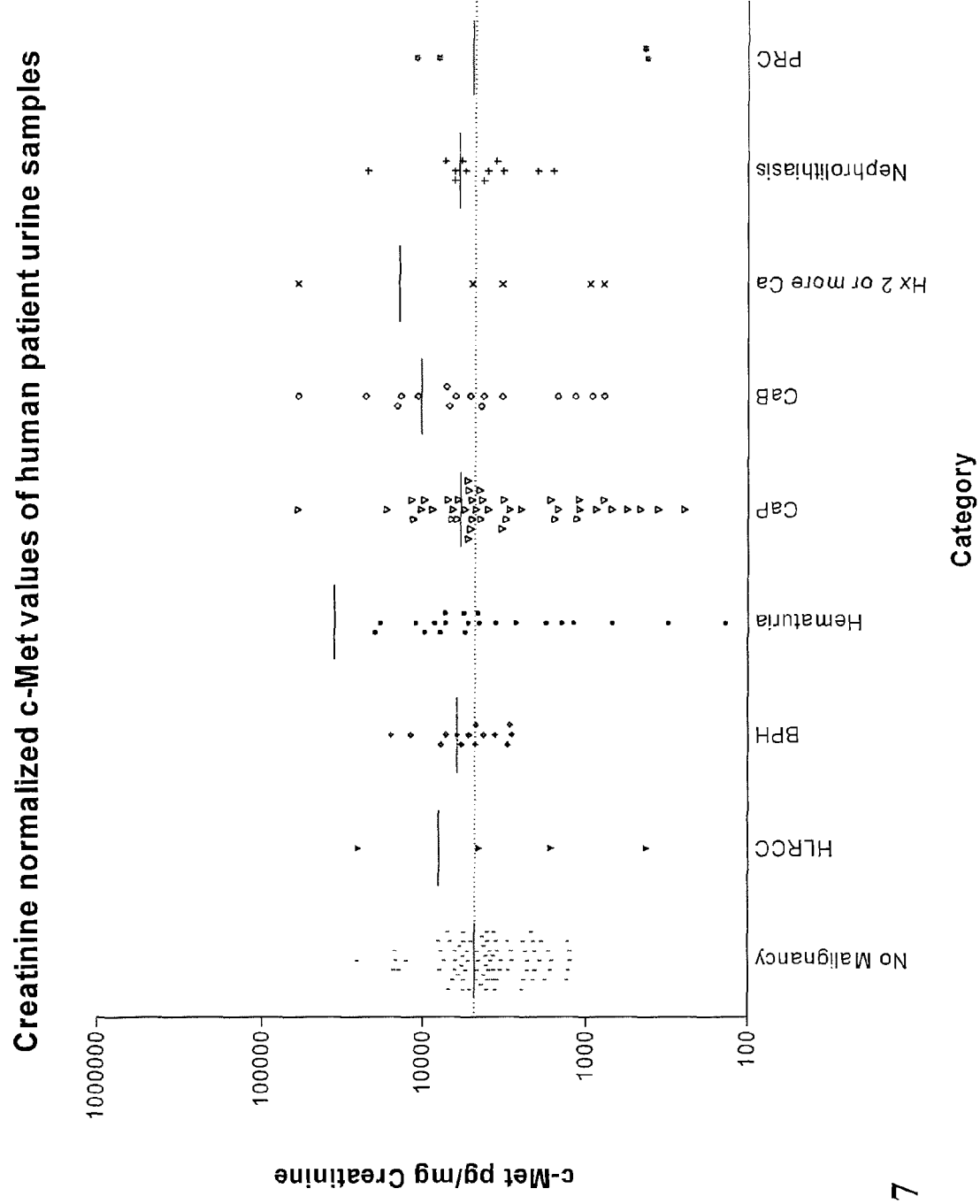
FIG. 7. Creatinine normalized c-Met values of human patient urine samples.
Figure 8:
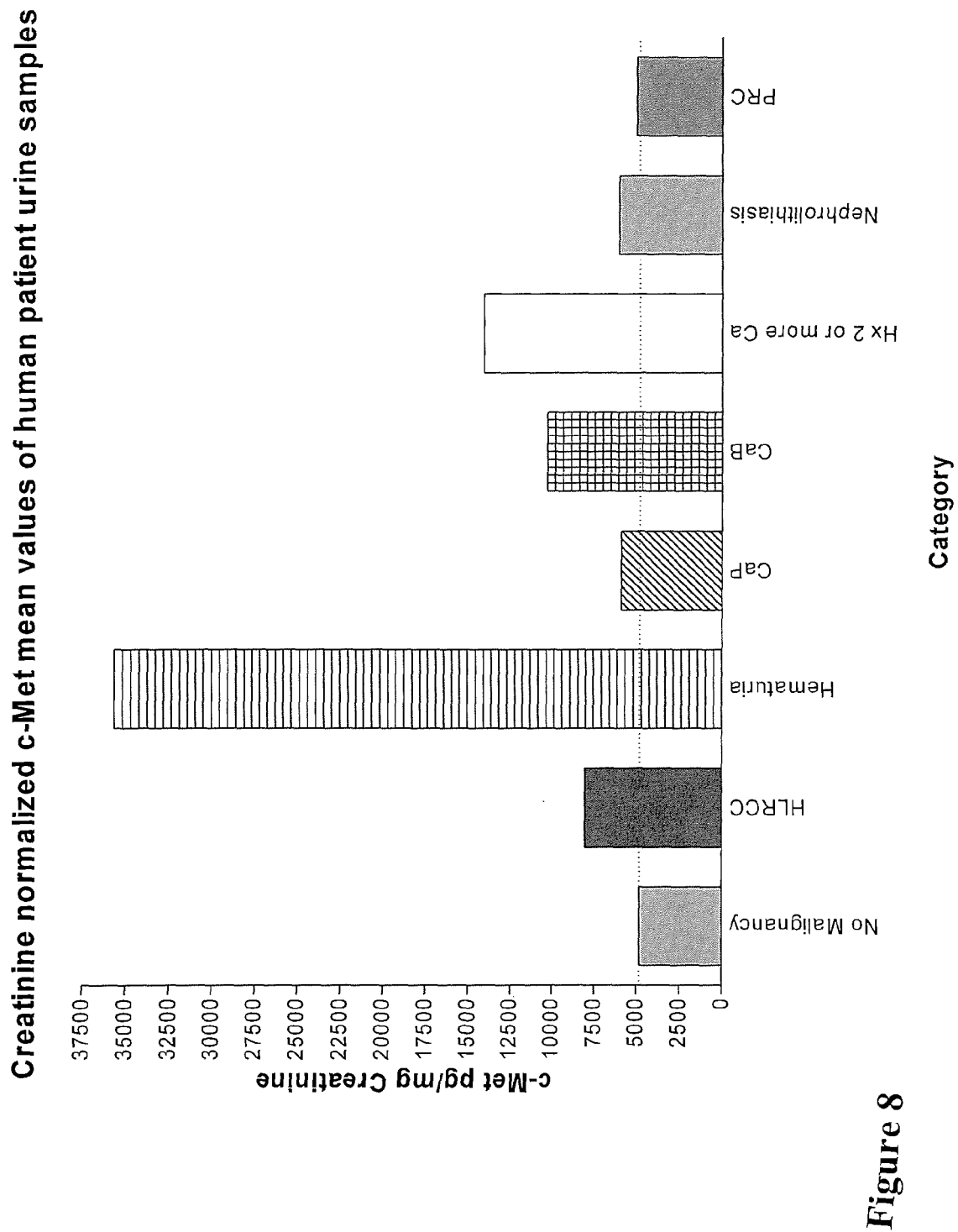
FIG. 8. Creatinine normalized c-Met mean values of human patient urine samples.
Figure 9:
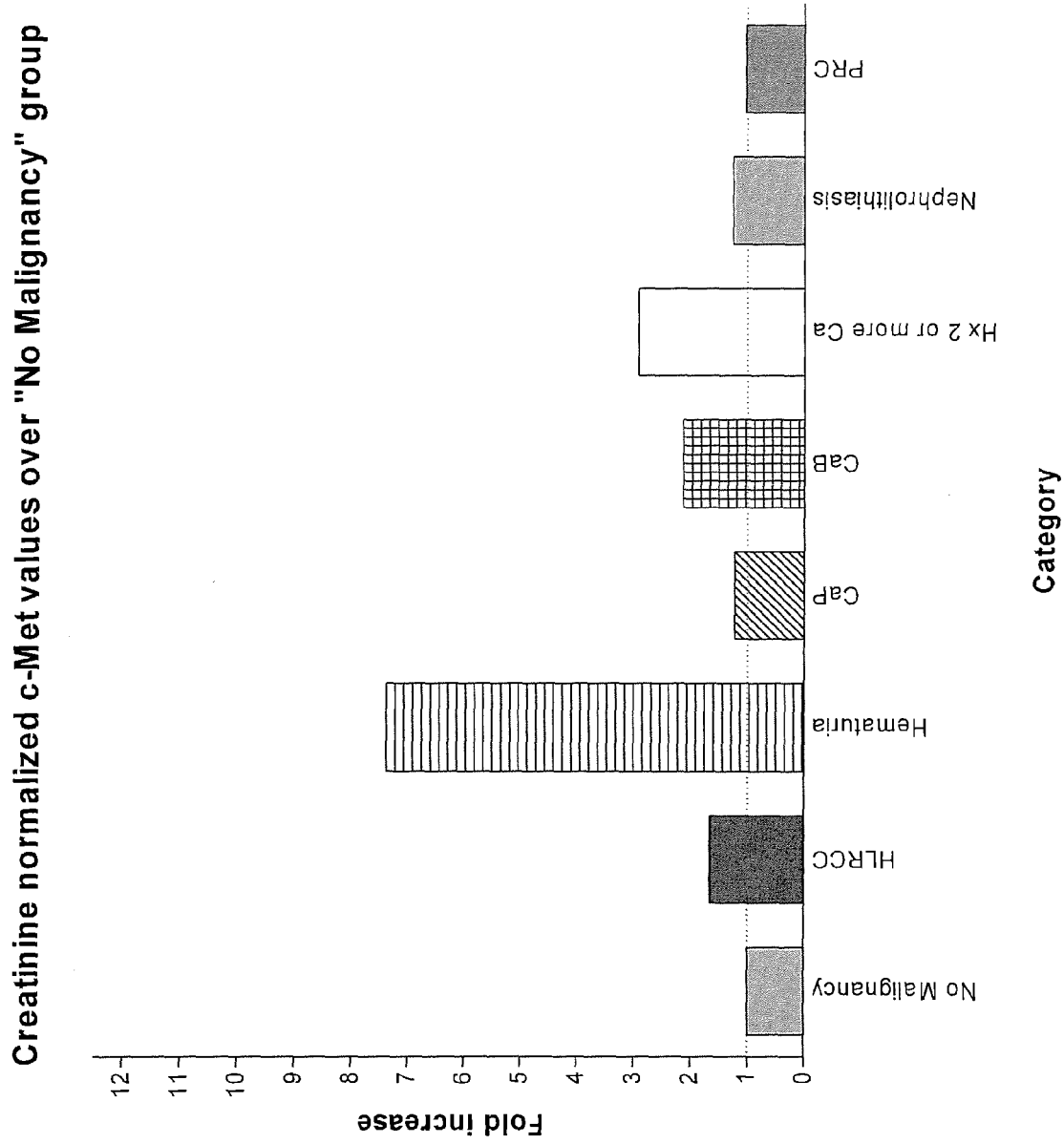
FIG. 9. Creatinine normalized c-Met values over "No Malignancy" group.

These results demonstrate that soluble c-Met produced by tumor derived cultured cell xenografts can be detected in plasma at very early stages of tumorigenesis, and that urinary c-Met concentration is a reliable indicator of the soluble c-Met level in plasma. These data further support the overall fidelity of c-Met shedding as an index of malignant phenotype, tumor progression and tumor burden in c-Met expressing models of oncogenesis. The simplicity and sensitivity of the assay described here make it amenable to high throughput screening.

c-Met Shedding in a Group of Normal Patients and Patients with Cancers Delineated in FIGS. 7-9.

Soluble c-Met was measured in urine samples as described in for mouse urine, with the exception that the standard curve was generated in phosphate buffered normal saline, not pooled mouse urine. Urine creatinine was measured using a standard, commercially available spectrophotometric method which is routinely used in medical laboratories. Samples for all assays were performed in triplicate or quadruplicate. Prior to measurements, samples were centrifuged to remove cells and debris, filtered through 0.22 micron filters, and the pH was adjusted to 7.4.

c-Met Shedding in a Group of Normal Patients and Patients with Bladder Cancer.

Figure 12:
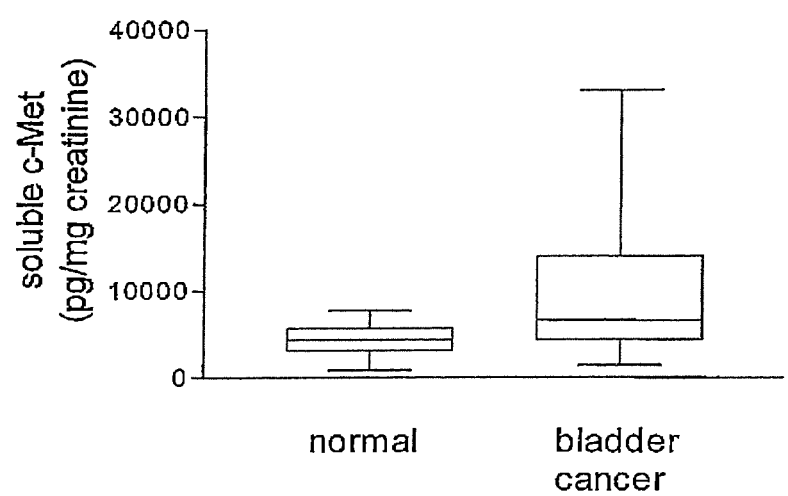
FIG. 12: c-Met in normal patients versus patients with bladder cancer.

Soluble c-Met was measured in urine samples as described in for mouse urine, with the exception that the standard curve was generated in phosphate buffered normal saline, not pooled mouse urine. Urine creatinine was measured using a standard, commercially available spectrophotometric method which is routinely used in medical laboratories. Samples for all assays were performed in triplicate or quadruplicate. Prior to measurements, samples were centrifuged to remove cells and debris, filtered through 0.22 micron filters, and the pH was adjusted to 7.4. Values of soluble c-Met were obtained from the raw data using the standard curve (run in every assay); the standard curve was generated as described, final values are expressed as pg/ml. Urine creatinine was also measured against a standard curve and values are expressed as mg/ml. Corrected c-Met/creatinine values are expressed as pg/mg. Statistical analysis was performed using GraphPad Prism software, using assumptions and conventions accepted throughout the research community. t-test at the $p<0.05$ level is the standard method for comparing the mean value obtained from patient replicates to the normal group mean, i.e. determining if any difference is unlikely to be due to chance. See FIG. 12.

Normals were healthy adult volunteers with no medical history of cancer and asymptomatic for diseases of the kidney, prostate, bladder or urinary tract at the time the sample was obtained, as established by routine medical laboratory tests, physical exam, and interview.

Bladder cancer samples were obtained from adult patients with biopsy proven (graded and staged by a licensed pathologist) bladder cancer or TCC (transitional cell carcinoma, which originates in ureteral epithelium, generally classified with bladder cancer). Patients had active or stable disease and samples were obtained prior to any surgical intervention.

Table 1 below provides the soluble c-Met measurements as pg per mg urine creatinine.

TABLE 1

| Statistics | Normals | Bladder Cancer |
| --- | --- | --- |
| Number of values | 30 | 12 |
| Minimum | 892.3 | 1498 |
| 25% Percentile | 3071 | 4343 |
| Median | 4344 | 6658 |
| 75% Percentile | 5719 | 13990 |
| Maximum | 7742 | 33090 |
| Mean | 4193 | 10600 |
| Standard Deviation | 1835 | 9278 |
| Standard Error | 335 | 2678 |
| Lower 95% Confidence Interval | 3508 | 4709 |
| Higher 95% Confidence Interval | 4878 | 16500 |
| KS Distance | 0.09099 | 0.2363 |
| P Value | P > 0.10 | P > 0.10 |

TABLE 1-continued

| Statistics | Normals | Bladder Cancer |
|---|---|---|
| Passed Normality Test (* = 0.05) | Yes | Yes |
| P Value Summary | ns | ns |
| Coefficient of Variation | 43.76% | 87.49% |
| Geometric mean | 3689 | 7644 |

Adaptation of the Soluble c-Met Immunoassay for Analysis of Human Plasma Samples.

Initial measurements of soluble c-Met in human plasma samples obtained from normal healthy volunteers, using the recombinant 358-MT c-Met-Ig fusion protein (R&D Systems) as standard and the same assay protocol used for cultured cell supernatants, revealed very high soluble c-Met levels were present.

Experiments confirm that the measurements were reliable and not due to a factor present in plasma other than bona fide c-Met protein:

1. Samples of goat plasma and mouse plasma were measured to determine whether a plasma constituent other than c-Met might contribute to signal intensity. Because the assay reagents do not cross-react with c-Met protein from mouse or goat, any reading above background would be grounds to suspect a contributory factor in human plasma other than c-Met. Neither goat nor mouse samples displayed soluble c-Met reading above background.

2. Samples of human plasma were diluted with three different buffers over a four log range and then measured in the assay. In many cases, artifactual readings do not decrease linearly with dilution. Using Tris-HCl, PBS or de-ionized water, the signal present in human plasma directly in proportion to dilution factor.

3. Samples of human plasma were subjected to denaturing conditions (heating to 95° C. for 30 minutes) prior to measurement of soluble c-Met in that assay. Under these conditions, many plasma proteins are precipitated. Samples subjected to this protocol did not show c-Met readings above background.

4. Samples of human plasma were subjected to immunodepletion of c-Met prior to measurement in the assay. Ideally, repeated rounds of immunodepletion should remove soluble c-Met from the sample, reducing the measured value to background levels. The protocol used and results obtained from a representative experiment are shown below. To control for the non-specific removal of c-Met from the sample by the protein G beads used to capture immunocomplexes, a mock immunodepletion was performed on human plasma samples in parallel which using a goat-derived IgG directed against a protein not present in human plasma.

5. Samples of human plasma subjected to immunodepletion were analyzed by SDS-PAGE and immunoblotting with another anti-c-Met antibody not used in the immunoassay. A standard curve of 358-MT samples were run in parallel to estimate the amount of soluble c-Met present. Results were consistent with the immunodepletion experiments shown below (data not shown). Crude estimates of soluble c-Met in human plasma based on immunoblotting were in the range of 100 ng/ml.

Protocol for Immunodepletion (ID) of Soluble c-Met from Human Plasma:

1. To 5 ml human plasma add anti-c-Met R&D AF276 (1 .mu.g/ml of plasma) and incubate on ice for 1 hour; agitate gently every 15 min. In parallel for MOCK samples, add Goat IgG (Rockland) at the same concentration. Repeat all subsequent steps with both ID and MOCK samples.

2. Add Protein G-Sepharose (Amersham; 30 μl/ml plasma) and rotate at 4 C for 1 hour.

3. Spin at 3000 rpm at 4° C. 1-2 minutes in Eppendorf desktop centrifuge to pellet beads. Remove supernatant. Take sample from supernatant (store on ice) and repeat steps 1-3 three more times for a total of four immunodepletion steps.

Figure 13:
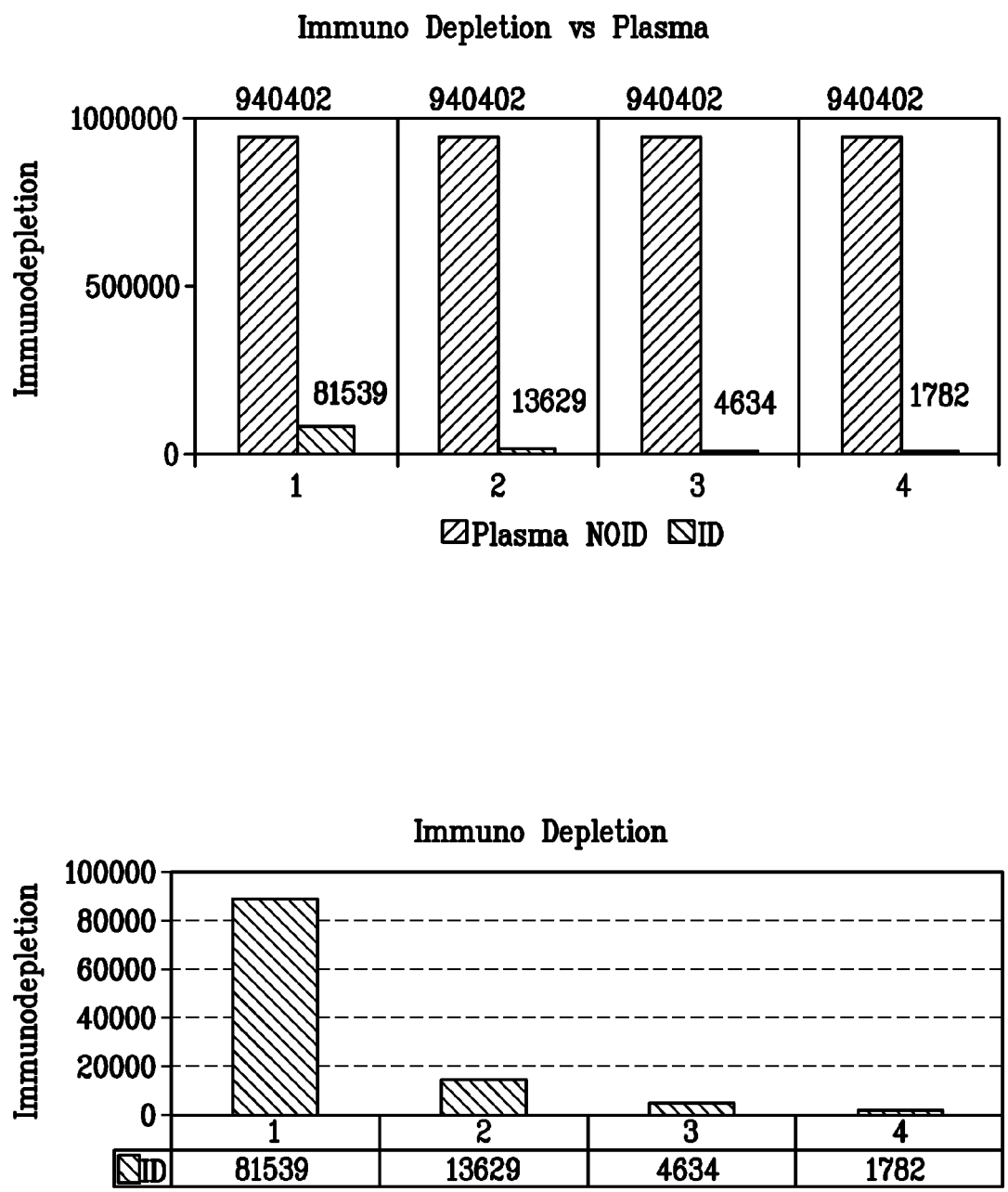
FIG. 13: Immunodepletion of plasma samples.

In FIG. 13, the upper panel shows rounds 1 through 4 of immunodepletion on the category (x) axis, and signal strength in the assay on the Y-axis. The undepleted plasma samples value is shown as a blue bar next to each round of immunodepletion. Signal values are listed numerically above each bar. Background value is approximately 1500 units. The bottom panel shows the immunodepletion samples alone to better visualize the degree of depletion. Variation between triplicate samples is consistent less than 2%.

The results of all experiments support the conclusion that 100% of the signal generated by assay of soluble c-Met in plasma represent bona fide c-Met protein. Measurement of soluble c-Met protein in human plasma samples obtained from a small set of healthy volunteers suggests that the normal concentration range is approximately 100 ng/ml. Analysis of a larger sample set is underway. Given the sensitivity of the assay and the initial concentration estimate, it should be possible to dilute plasma samples 100-fold prior to measurement, using approximately 100 microliters of final volume per well. This should allow replicates of 4 to 6 wells/sample to be generated from very small (10 microliter) plasma samples.

From the foregoing description, various modifications and changes in the compositions and methods will occur to those skilled in the art. All such modifications coming within the scope of the appended claims are intended to be included therein. Each recited range includes all combinations and sub-combinations of ranges, as well as specific numerals contained therein.

All publications and patent documents cited above are hereby incorporated by reference in their entirety for all purposes to the same extent as if each were so individually denoted.

Although the foregoing invention has been described in detail by way of example for purposes of clarity of understanding, it will be apparent to the artisan that certain changes and modifications are comprehended by the disclosure and can be practiced without undue experimentation within the scope of the appended claims, which are presented by way of illustration not limitation.

What is claimed is:

1. A method of monitoring the status of cancer in a patient comprising:
   determining the concentration of soluble c-Met ectodomain in a first biological tissue from the patient at a first time point,
   determining the concentration of soluble c-Met ectodomain in a second biological tissue from the patient at a second time point that is later than the first time point, wherein the first and second biological tissues are the same type of tissues, and
   determining the status of cancer in the patient by comparing the concentration of soluble c-Met ectodomain in the first and second biological tissues
   wherein a difference in the concentration of soluble c-Met ectodomain in the first and second biological tissues indicates that the patient's cancer has regressed or worsened; and
   wherein similar concentrations of soluble c-Met ectodomain in the first and second biological tissues indicates that the patient's cancer has remained stable; and
   wherein a lower concentration of soluble c-Met ectodomain in the second biological tissue than that in the first biological tissue indicates that the patient's cancer has regressed; and
   wherein a greater concentration of soluble c-Met ectodomain in the second biological tissue than that in the first biological tissue indicates that the patient's cancer has worsened.

2. The method of claim 1 further comprising determining the concentration of soluble c-Met ectodomain in one or more additional biological tissues of the same type as the first and second biological tissues at time points that are progressively later than the second time point.

3. The method of claim 1 where in the cancer is metastatic cancer.

4. The method of claim 1 wherein the cancer is a cancer of the urinary tract.

5. The method of claim 4 wherein the cancer is kidney cancer, renal cancer, bladder cancer, or renal cell carcinoma.

6. The method of claim 5 wherein the cancer is bladder cancer.

7. The method of claim 1 wherein the cancer is prostate cancer.

8. The method of claim 1 wherein the cancer is breast cancer.

9. A method for measuring a patient's response to cancer therapy comprising:
   determining the concentration of soluble c-Met ectodomain in a biological tissue from the patient at a first time point,
   determining the concentration of soluble c-Met ectodomain in a second biological tissue from the patient at a second time point that is later than the first time point, wherein the first and second biological tissues are the same type of tissues, and
   determining the patient's response to cancer therapy by comparing the concentration of soluble c-Met ectodomain in the first and second biological tissues
   wherein a difference in the concentration of soluble c-Met ectodomain in the first and second biological tissues indicates that the patient's cancer has regressed or worsened; and
   wherein similar concentrations of soluble c-Met ectodomain in the first and second biological tissues indicates that the patient has not responded to the cancer therapy; and
   wherein a lower concentration of soluble c-Met ectodomain in the second biological tissue relative to that in the first biological tissue indicates that the patient has responded positively to the cancer therapy; and
   wherein a greater concentration of soluble c-Met ectodomain in the second biological tissue than that in the first biological tissue indicates that the patient has not responded to the cancer therapy or has responded negatively to the cancer therapy.

10. The method of claim 9 further comprising determining the concentration of soluble c-Met ectodomain in one or more additional biological tissues of the same type as the first and second biological tissues at time points that are progressively later than the second time point.

11. The method of claim 9 wherein the cancer therapy is an anti-cancer drug.

12. The method of claim 11 wherein the drug is a chemotherapeutic agent.

13. The method of claim 9 wherein the cancer therapy is ionizing radiation therapy or hormone ablation therapy.

14. The method of claim 9 where in the cancer is metastatic cancer.

15. The method of claim 9 wherein the cancer is a cancer of the urinary tract.

16. The method of claim 15 wherein the cancer is kidney cancer, renal cancer, bladder cancer, or renal cell carcinoma.

* * * * *